US010519193B2

(12) United States Patent
Wang et al.

(10) Patent No.: US 10,519,193 B2
(45) Date of Patent: Dec. 31, 2019

(54) STEROIDAL COMPOUND, COMPOSITION CONTAINING THE SAME AND USE THEREOF

(71) Applicant: Shenzhen TargetRx, Inc., Shenzhen (CN)

(72) Inventors: Yihan Wang, Shenzhen (CN); Xingye Ren, Shenzhen (CN)

(73) Assignee: Shenzhen TargetRx, Inc., Shenzhen, Guangdong (CN)

( * ) Notice: Subject to any disclaimer, the term of this patent is extended or adjusted under 35 U.S.C. 154(b) by 0 days.

(21) Appl. No.: 16/074,727

(22) PCT Filed: Dec. 29, 2016

(86) PCT No.: PCT/CN2016/112945
§ 371 (c)(1),
(2) Date: Aug. 1, 2018

(87) PCT Pub. No.: WO2017/133360
PCT Pub. Date: Aug. 10, 2017

(65) Prior Publication Data
US 2019/0040098 A1    Feb. 7, 2019

(30) Foreign Application Priority Data

Feb. 2, 2016  (CN) .......................... 2016 1 0092378

(51) Int. Cl.
A61P 35/00    (2006.01)
C07J 43/00    (2006.01)
C07J 1/00     (2006.01)
C07J 13/00    (2006.01)
C07J 41/00    (2006.01)

(52) U.S. Cl.
CPC ............. C07J 43/003 (2013.01); A61P 35/00 (2018.01); C07B 2200/05 (2013.01); C07J 1/0011 (2013.01); C07J 13/005 (2013.01); C07J 41/0005 (2013.01)

(58) Field of Classification Search
CPC ......... C07J 43/003; A61K 31/58; A61P 35/00
See application file for complete search history.

(56) References Cited

U.S. PATENT DOCUMENTS 6,221,335 B1 * 4/2001 Foster ................... C07B 59/002
                                                  424/1.81
6,440,710 B1 * 8/2002 Keinan .................. C12P 13/02
                                                  435/147
6,603,008 B1 * 8/2003 Ando .................... C07D 405/14
                                                  546/269.7
7,517,990 B2 * 4/2009 Ito ........................ C07B 59/002
                                                  546/184
2007/0082929 A1 * 4/2007 Gant .................... C07D 401/12
                                                  514/338
2007/0197533 A1 * 8/2007 Zhou .................... C07D 401/04
                                                  514/241
2007/0197695 A1 * 8/2007 Potyen ................. C08K 5/0091
                                                  524/110

FOREIGN PATENT DOCUMENTS

JP       H07-505377 A      6/1995
JP       2013-545815 A    12/2013
WO       WO 93/20097 A1   10/1993
WO       WO 2010/054158 A2  5/2010
WO       WO 2012/083112 A2  6/2012
WO       WO 2013/192097 A1 12/2013
WO       WO 2014/083512 A1  6/2014
WO       WO 2015/000451 A1  1/2015

OTHER PUBLICATIONS

Dyck, Journal of Neurochemistry vol. 46 Issue 2, pp. 399-404 (1986).*
Tonn, Biological Mass Spectrometry vol. 22 Issue 11, pp. 633-642 (1993).*
Haskins, Biomedical Spectrometry vol. 9 Issue 7, pp. 269-277 (1982).*
Wolen, Journal of Clinical Pharmacology (1986); 26:419-424.*
Browne, Journal of Clinical Pharmacology (1998); 38:213-220.*
Baillie, Pharmacology Rev.(1981); 33:81-132.*
Gouyette, Biomedical and Environmental Mass Spectrometry, vol. 15, 243-247 (1988).*
Cherrah, Biomedical and Environmental Mass Spectrometry vol. 14 Issue 11, pp. 653-657 (1987).*
Pieniaszek, J Clin Pharnnacol.(1999); 39:817-825.*
Honma et al., Drug Metab Dispos 15 (4): 551 -559 (1987).*
Branden et al., Structure-based ligand design to overcome CYP inhibition in drug discovery projects, Drug Discovery Today, vol. 19, No. 7, pp. 905-911 (Jul. 2014).*
Simone, Oncology: Introduction, Cecil Textbook of Medicine, 20th Edition, vol. 1, pp. 1004-101 O, (1996).*
Johnson et al., Relationships between drug activity in NCI preclinical in vitro and in vivo models and early clinical trials, British Journal of Cancer, 84(10):1424-1431, (2001).*
Gura et al., Systems for identifying new drugs are often faulty, Science, 278:1041-1042, (1997).*
Bundgaard, Design of Prodrugs, p. 1, 1985.*
Silverman, Prodrugs and Drug Delivery Systems, The Organic Chemistry of Drug Design and Drug Action, pp. 352-399, 1992.*
Fura, A., Role of pharmacologically active metabolites in drug discovery and development, DDT, 2006, 11, pp. 133-142.*

(Continued)

Primary Examiner — Deepak R Rao
(74) Attorney, Agent, or Firm — Wolf, Greenfield & Sacks, P.C.

(57) ABSTRACT

Disclosed are a steroidal compound as shown in formula (I) and a drug composition containing the same, or a crystal form, a pharmaceutically acceptable salt, a hydrate or solvate, a stereoisomer, a prodrug, a metabolite or an isotopic variant thereof. The compound can be used as a CYP17 enzyme inhibitor, and has better pharmacokinetic parameters, which can improve drug concentration of the compound in an animal, thereby improving the efficacy and safety of the drug, and in turn the compound may be applied in the preparation of the drug for treating CYP17 enzyme-related diseases (such as prostate cancer).

14 Claims, No Drawings

(56) References Cited

OTHER PUBLICATIONS

Anari et al., Bridging cheminformatic metabolite prediction and tandem mass spectrometry, DDT, 2005, vol. 10, No. 10, pp. 711-717.*

Nedderman, A.N.R., Metabolites in safety testing: Metabolite Identification Strategies in Discovery and Development, Biopharm. Drug Depos. 2009, 30, pp. 153-162.*

Brossard et al., N-substituted piperazinopyridylsteroid derivatives as abiraterone analogues inhibit growth and induce pro-apoptosis in human hormone-independent prostate cancer cell lines. Chem Biol Drug Des. Nov. 2013;82(5):620-9. doi:10.1111/cbdd.12195.

Katsnelson, Heavy drugs draw heavy interest from pharma backers. Nat Med. Jun. 2013;19(6):656. doi: 10.1038/nm0613-656.

Nagase et al., 4-Position-Selective C-H Perfluoroalkylation and Perfluoroarylation of Six-Membered Heteroaromatic Compounds. J Am Chem Soc. May 18, 2016;138(19):6103-6. doi: 10.1021/jacs. 6b01753. Epub May 6, 2016.

Declaration under 37 CFR § 1.132. Vinita Uttamsingh. Apr. 14, 2008.

Harbeson et al., Deuterium in Drug Discovery and Development. Ann Rep Med Chem. 2011;46:403-417.

Shao et al., Derivatives of tramadol for increased duration of effect. Bioorg Med Chem Lett. 2006;16:691-694.

Extended European Search Report for EP Application No. 16889166.1 dated Jan. 31, 2019.

Li et al., Conversion of abiraterone to D4A drives anti-tumour activity in prostate cancer. Nature. Jul. 16, 2015;523(7560)347-51. doi: 10.1038/nature14406. Epub Jun. 1, 2015.

Stappaerts et al., Rapid conversion of the ester prodrug abiraterone acetate results in intestinal supersaturation and enhanced absorption of abiraterone: in vitro, rat in situ and human in vivo studies. Eur J Pharm Biopharm. Feb. 2015;90:1-7. doi: 10.1016/j.ejpb.2015.01. 001. Epub Jan. 12, 2015.

PCT/CN2016/112945, Apr. 12, 2017, International Search Report and Written Opinion.

PCT/CN2016/112945, Aug. 16, 2018, International Preliminary Report on Patentability.

Foster, Deuterium Isotope Effects in the Metabolism of Drugs and Xenobiotics: Implications for Drug Design. Advances in Drug Research. 1985;14;2-39.

Shao et al., The kinetic isotope effect in the search for deuterated drugs. Drug News Perspect. Jul. 2010-Aug.;23(6):398-404. doi: 10.1358/dnp.2010.23.6.1426638.

* cited by examiner

STEROIDAL COMPOUND, COMPOSITION CONTAINING THE SAME AND USE THEREOF

CROSS REFERENCE TO RELATED APPLICATIONS

This application is a national stage filing under 35 U.S.C. 371 of International Patent Application Serial No. PCT/CN2016/112945, filed Dec. 29, 2016, entitled "STEROIDAL COMPOUND, COMPOSITION CONTAINING THE SAME AND USE THEREOF," which claims priority to Chinese patent application number 201610092378.8, filed Feb. 2, 2016, the entire content of each of which is incorporated herein by reference in its entirety.

TECHNICAL FIELD

The disclosure belongs to the pharmaceutical field. In particular, disclosed herein are steroidal compounds and the use thereof, and more particularly, steroidal compounds and the use thereof as irreversible inhibitors of CYP17 enzyme, or the use in the treatment and prevention of CYP17-related diseases.

BACKGROUND OF THE INVENTION

Prostate cancer (PCa) is a common malignancy in the male reproductive system. In 2008, there were 903,500 new cases of prostate cancer and 258,400 deaths due to prostate cancer globally. Among them, new cases of prostate cancer account for 14% of all new cases of male tumors, ranking 2nd in new cases of male tumors; deaths due to prostate cancer account for 6% deaths of male cancers, ranking 6th in deaths of male cancers. Deaths due to prostate cancer account for 9% deaths of male cancers, ranking 2nd in deaths of male cancers following lung cancer. Due to the deterioration of environmental pollution in recent years, accelerated aging of the population, and changes in people's dietary patterns, the incidence and mortality of prostate cancer have increased rapidly. Now the prostate cancer has become one of the important diseases affecting the male health in China.

The effect of androgen on the growth of prostate cancer cells is mediated by androgen receptor (AR) signaling pathway. Clinically, the level of prostate-specific antigen (PSA) in patients is observed by changes in AR signal, thereby patients with prostate cancer are diagnosed and treated. Traditional castration therapy does not completely inhibit the production of androgens or the expression of the target gene of androgen receptor. When the androgen synthase is overexpressed, the level of androgens in the tumor will increase.

Cytochrome oxidase P450 c17 (CYP17) is expressed in the testis, adrenal gland and normal prostate tissues, and it is also expressed in prostate cancer cells. 17α-hydroxylase and C17,20-lyase in CYP17 are key enzymes in androgen biosynthesis, which can promote the conversion of steroid progesterone and pregnenolone into C19 androstenedione and dehydroepiandrosterone, respectively, and both in turn are converted into testosterone and dihydrotestosterone (DHT).

Based on the above studies, the prevention and treatment of prostate cancer is an urgent task. Researching and developing inhibitors of CYP17 enzyme is an important direction for drug treatment of prostate cancer. As a novel inhibitor of CYP17 enzyme, abiraterone acetate was developed by Centocor Ortho to treat prostate cancer. Abiraterone acetate was approved by the FDA on Apr. 28, 2011, and was used in combination with prednisone to treat castration-resistant prostate cancer under the trade name Zytiga. On Jul. 28, 2011, Zytiga was approved by the Health Ministry of Canada. For patients with prostate cancer, hormone testosterone stimulates the growth of the tumor. Castration therapy, including medication or surgery, can reduce testosterone production or block testosterone, but this treatment does not inhibit the production of androgens in other parts of the body. Prostate cancer can still continue to grow. Abiraterone targetedly inhibits the activity of the CYP17 enzyme that regulates androgen production, reducing the production of androgens and slowing tumor growth. Median survival for patients treated with abiraterone acetate plus prednisone is 3.9 months longer than that of patients treated with placebo plus prednisone (14.8 and 10.9 months, respectively, p<0.0001), i.e., the risk of death is reduced by 35%. The common adverse effects are mineralocorticoid-related risk events, including urinary retention, hypokalemia, and hypertension.

However, abiraterone resistance has emerged during the treatment of prostate cancer. Therefore, there is still a need to develop more active and potent drugs for prostate cancer.

SUMMARY OF THE INVENTION

In view of the above problems, disclosed herein are a series of novel compounds having the effect of irreversible inhibitors of CYP17, which have excellent inhibitory properties against the CYP17 enzyme and also have better pharmacodynamic/pharmacokinetic properties.

In this regard, the technical solution adopted herein is: a substituted steroidal compound represented by Formula (I)

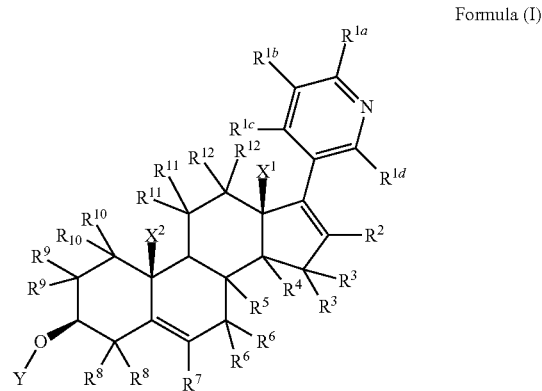

Formula (I)

wherein:
$R^{1a}, R^{1b}, R^{1c}, R^{1d}, R^2, R^3, R^4, R^5, R^6, R^7, R^8, R^9, R^{10}, R^{11}$, and $R^{12}$ are each independently hydrogen, deuterium, halogen, or trifluoromethyl;

$X^1$ and $X^2$ are independently selected from the group consisting of hydrogen (H), deuterium (D), methyl, $CH_2D$, $CHD_2$, $CD_3$, $CH_2CH_3$, $CHDCH_3$, $CHDCH_2D$, $CHDCHD_2$, $CHDCD_3$, $CD_2CH_3$, $CD_2CH_2D$, $CD_2CHD_2$, and $CD_2CD_3$;

Y is selected from hydrogen (H), deuterium (D), acetyl, and an acetyl group substituted with one or more deuteriums;

and physiologically acceptable salts, prodrugs, metabolites, solvates, tautomers and stereoisomers thereof, including mixtures of these compounds in all ratios.

In another embodiment, the content of deuterium isotope in the deuterated position is at least greater than the natural content of deuterium isotope (0.015%), preferably greater than 30%, more preferably greater than 50%, more preferably greater than 75%, more preferably greater than 95%, and more preferably greater than 99%.

In another embodiment, $R^{1a}$, $R^{1b}$, $R^{1c}$, and $R^{1d}$ are each independently deuterium or hydrogen.

In another embodiment, $R^2$, $R^3$, $R^4$, $R^5$, $R^6$, $R^7$, $R^8$, $R^9$, $R^{10}$, $R^{11}$ and $R^{12}$ are each independently deuterium or hydrogen.

In another embodiment, $X^1$ and $X^2$ may be independently selected from an alkyl group substituted with one or more deuteriums.

In another embodiment, Y is selected from hydrogen, deuterium, and an acetyl group substituted with one or more deuteriums.

In another embodiment, wherein $R^{1a}$, $R^{1b}$, $R^{1c}$, and $R^{1d}$ are deuterium.

In another embodiment, wherein $R^2$ is deuterium.
In another embodiment, wherein $R^3$ is deuterium.
In another embodiment, wherein $R^4$ is deuterium.
In another embodiment, wherein $R^5$ is deuterium.
In another embodiment, wherein $R^6$ is deuterium.
In another embodiment, wherein $R^7$ is deuterium.
In another embodiment, wherein $R^8$, $R^9$, and $R^{10}$ are deuterium.
In another embodiment, wherein $R^{11}$ and $R^{12}$ are deuterium.
In another embodiment, wherein $X^1$ and $X^2$ are methyl group substituted with three deuteriums.
In another embodiment, wherein Y is deuterium.
In another embodiment, wherein Y is an acetyl group substituted with three deuteriums.

In another embodiment, the compound is selected from, but not limited to, the following group of compounds or pharmaceutically acceptable salts thereof:

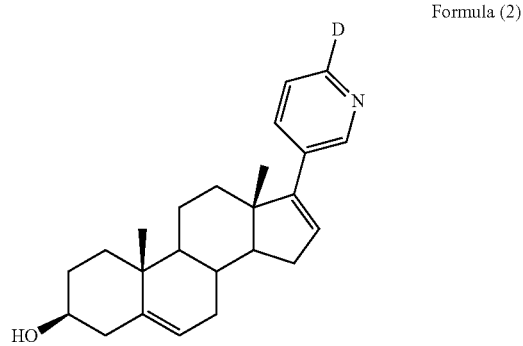

Formula (2)

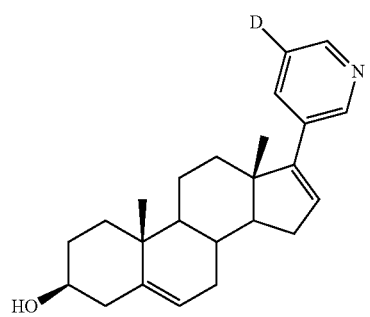

Formula (3)

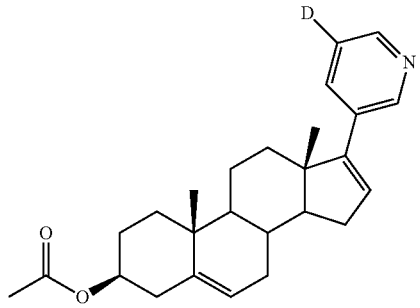

Formula (4)

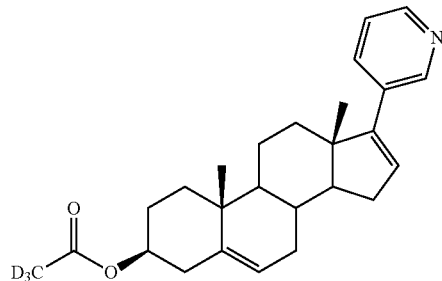

Formula (5)

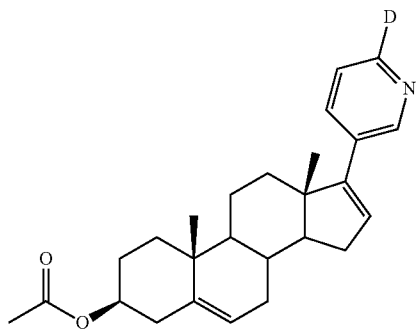

Formula (6)

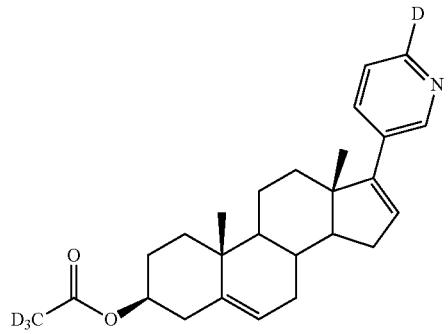

Formula (7)

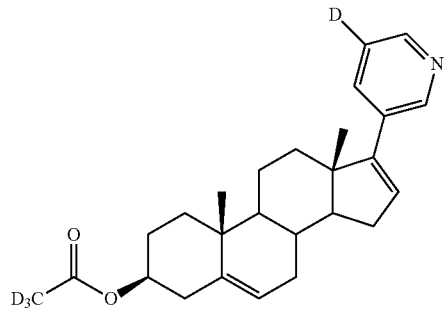

Formula (8)

-continued
Formula (9)
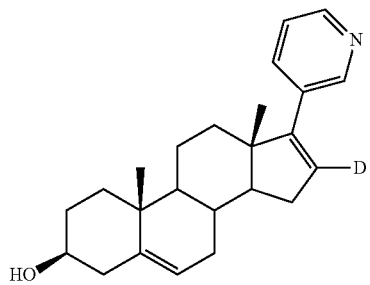
Formula (10)
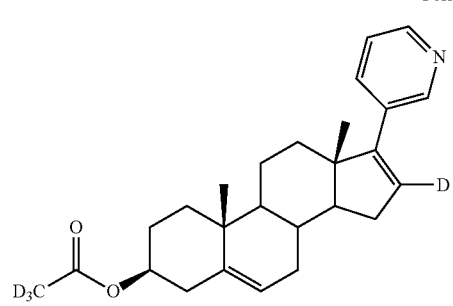
Formula (11)
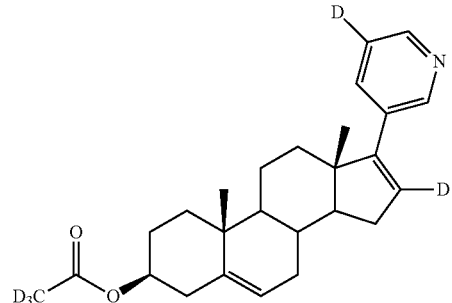
Formula (12)
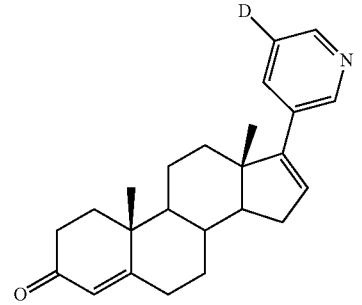
Formula (13)
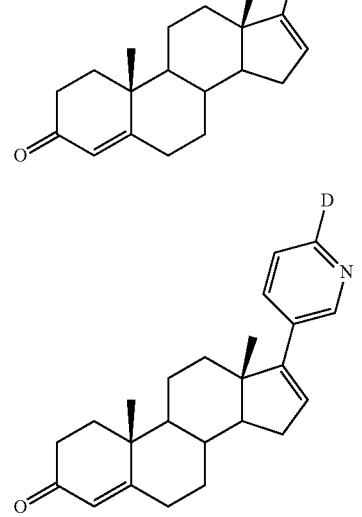
-continued
Formula (14)
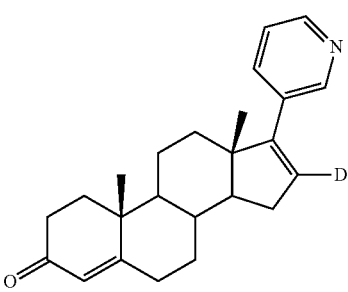
Formula (15)
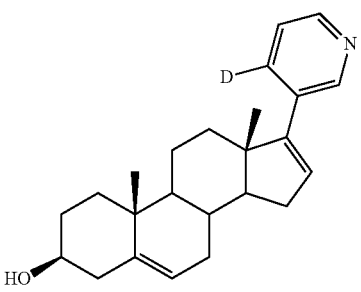
Formula (16)
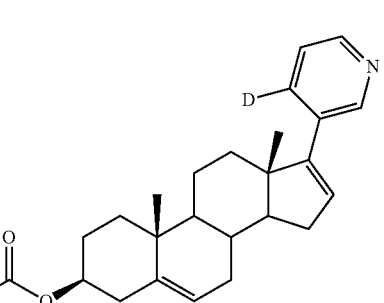
Formula (17)
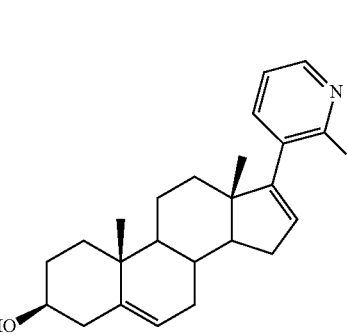
Formula (18)
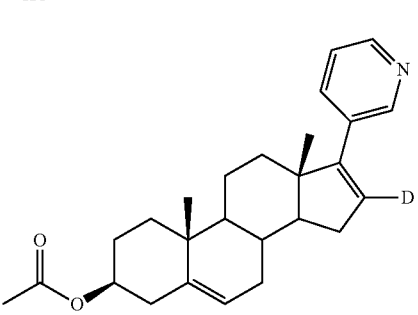

Formula (19)
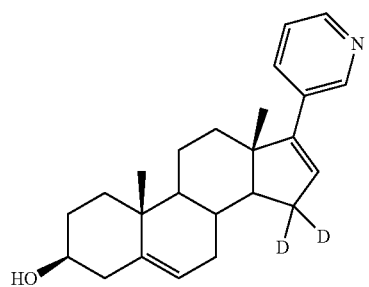
Formula (20)
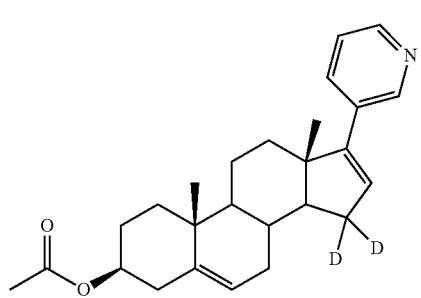
Formula (21)
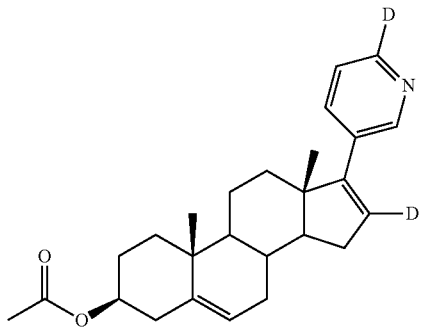
Formula (22)
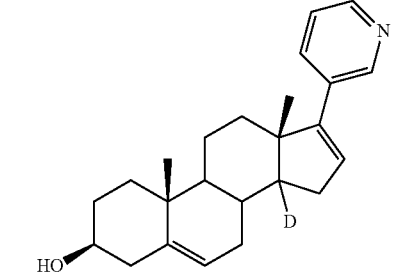
Formula (23)
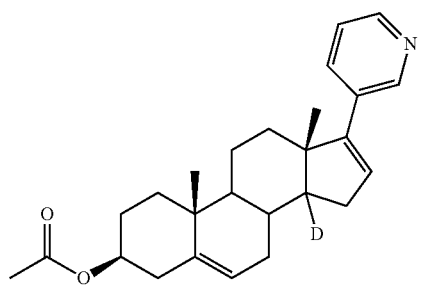
Formula (24)
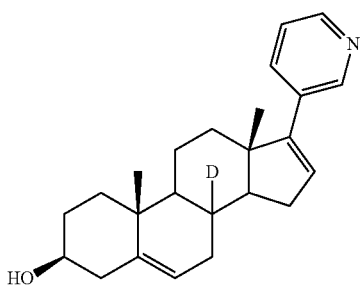
Formula (25)
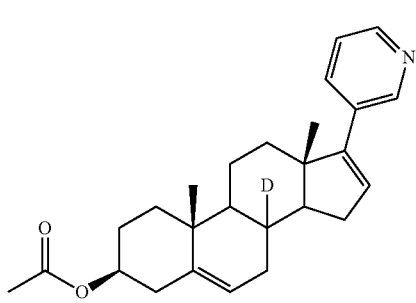
Formula (26)
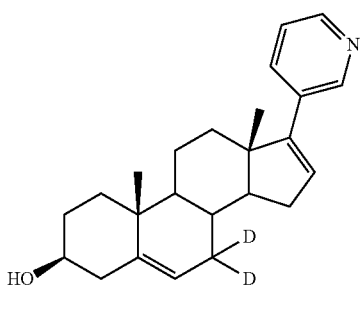
Formula (27)
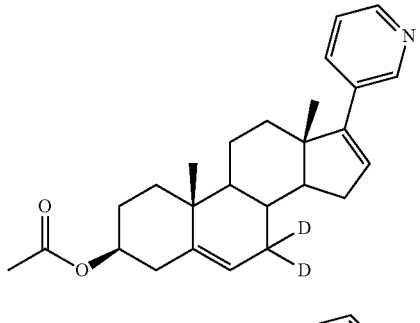
Formula (28)
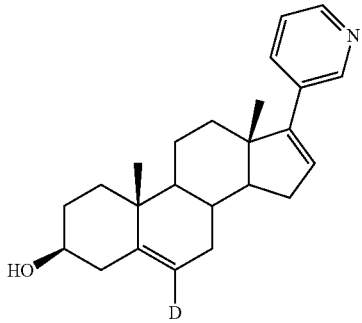

Formula (29)
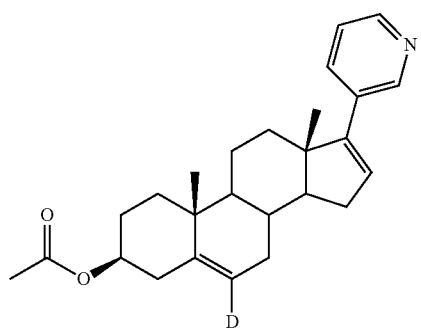
Formula (30)
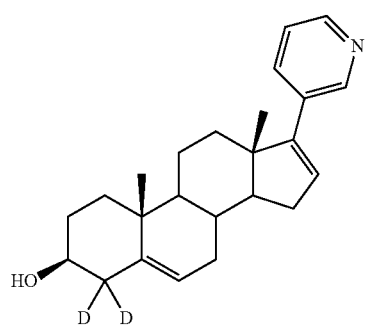
Formula (31)
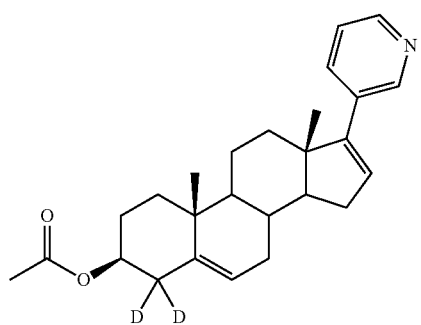
Formula (32)
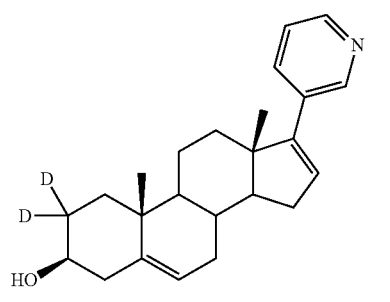
Formula (33)
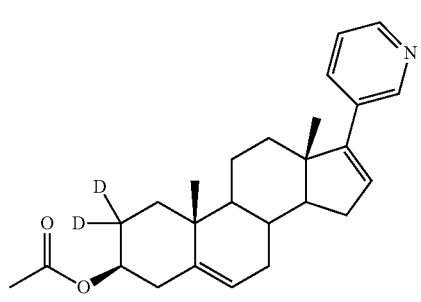
Formula (34)
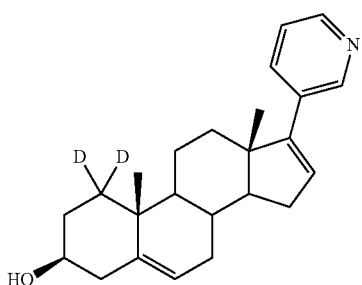
Formula (35)
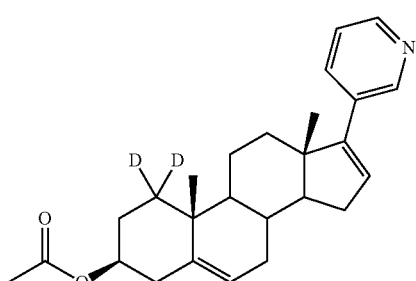
Formula (36)
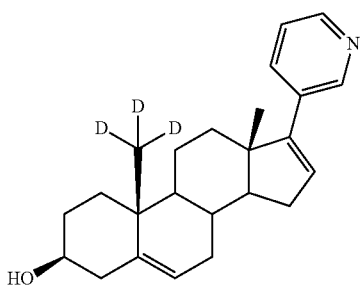
Formula (37)
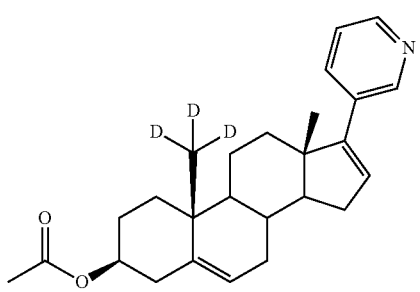
Formula (38)
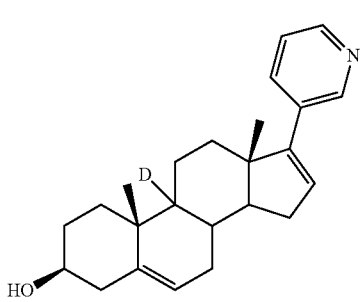

-continued
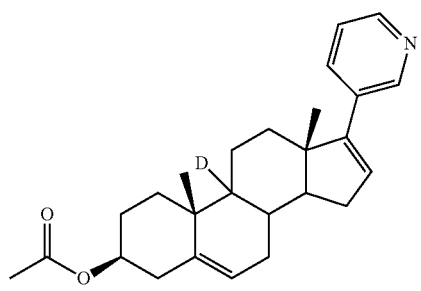
Formula (39)
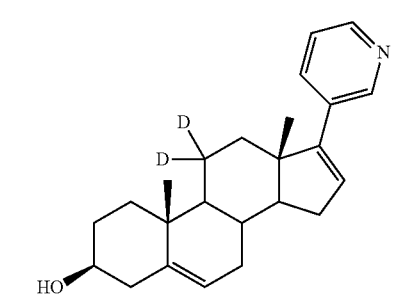
Formula (40)
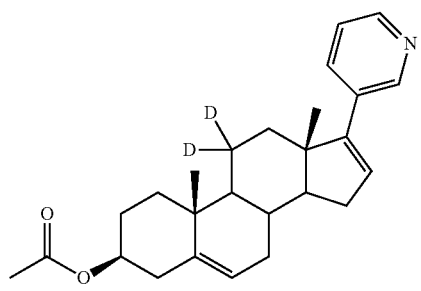
Formula (41)
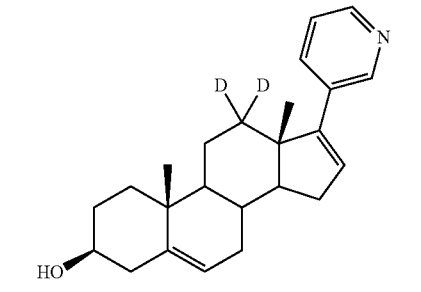
Formula (42)
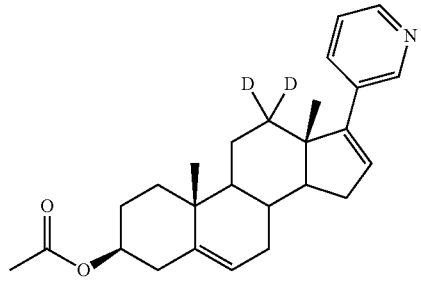
Formula (43)
-continued
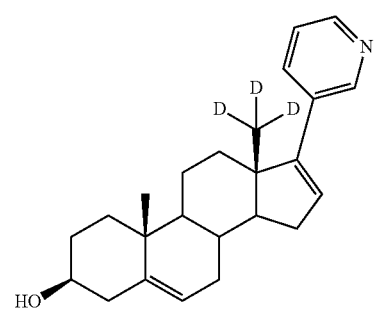
Formula (44)
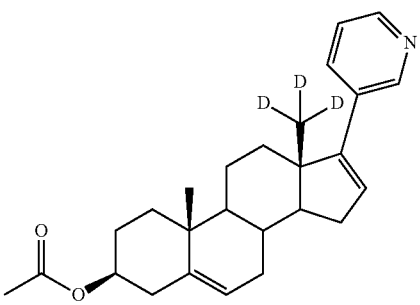
Formula (45)
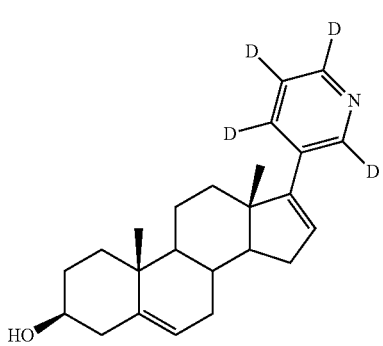
Formula (46)
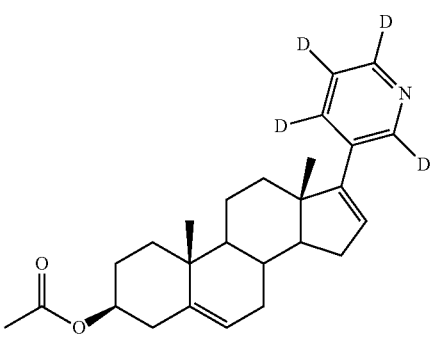
Formula (47)
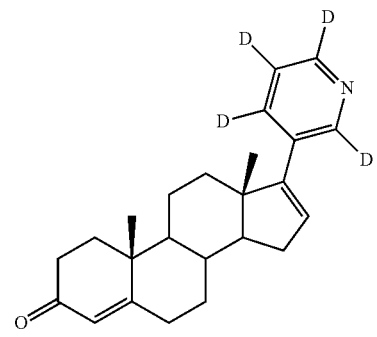
Formula (48)

Formula (49)
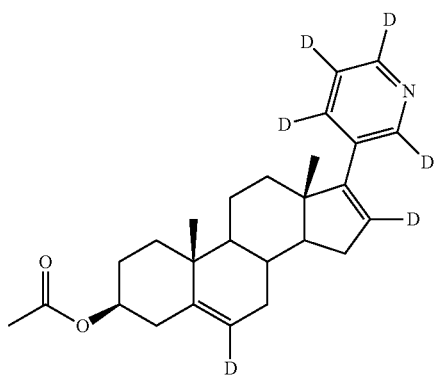
Formula (50)
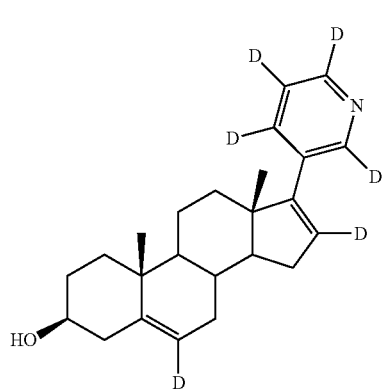
Formula (51)
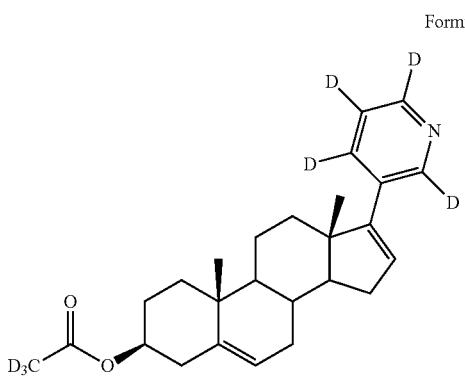
Formula (52)
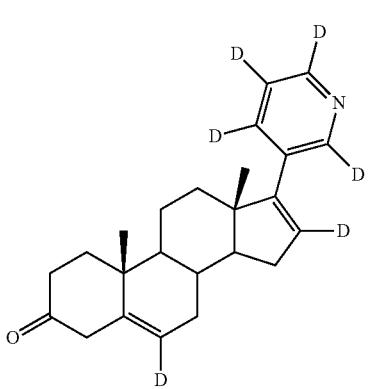
Formula (53)
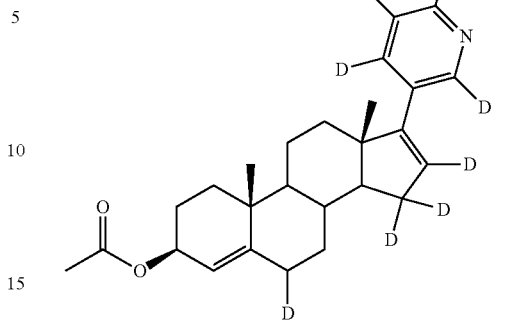
Formula (54)
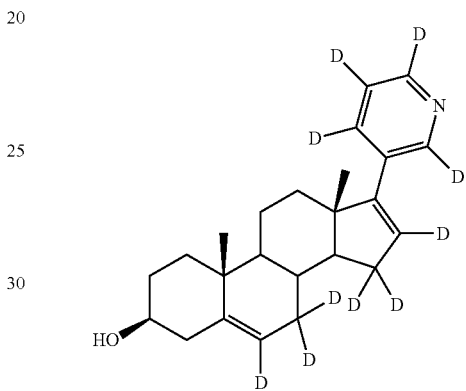
Formula (55)
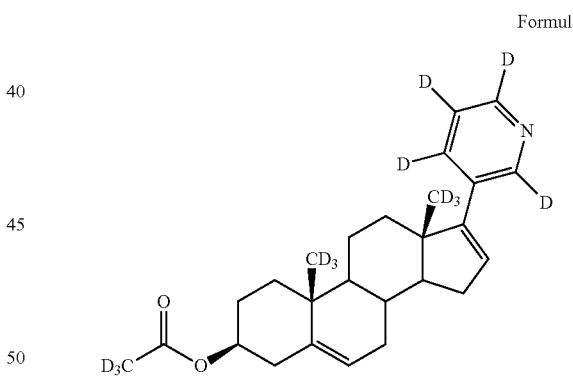
Formula (56)
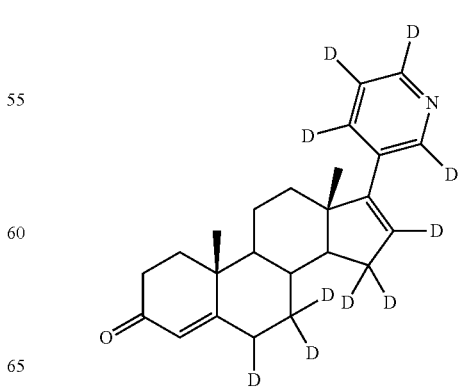

-continued
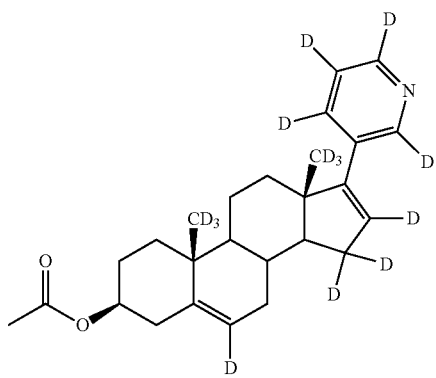
Formula (57)
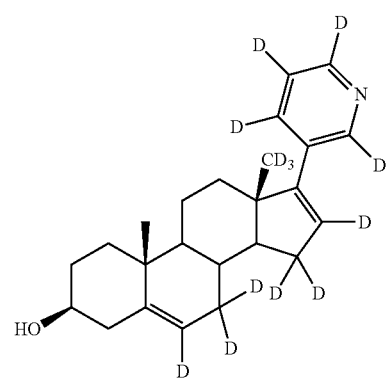
Formula (58)
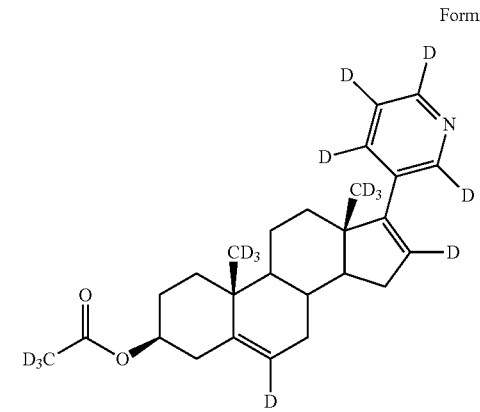
Formula (59)
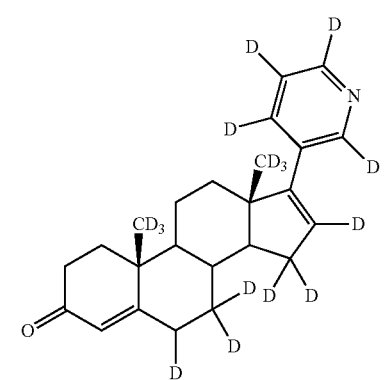
Formula (60)
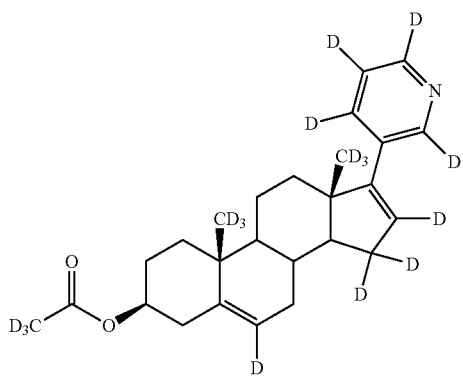
Formula (61)
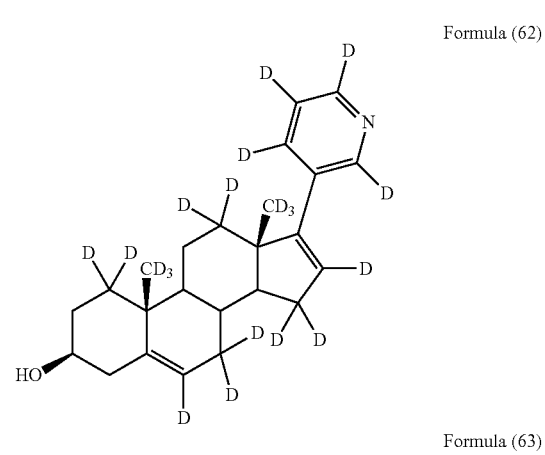
Formula (62)
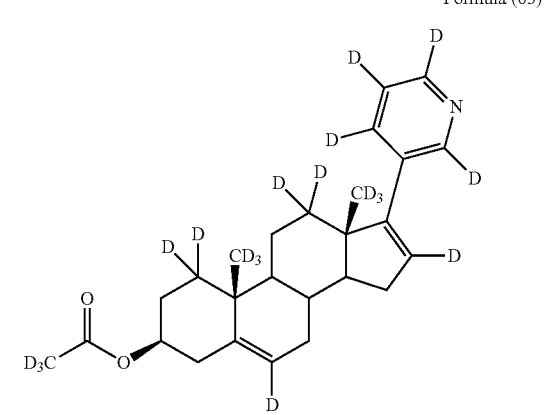
Formula (63)
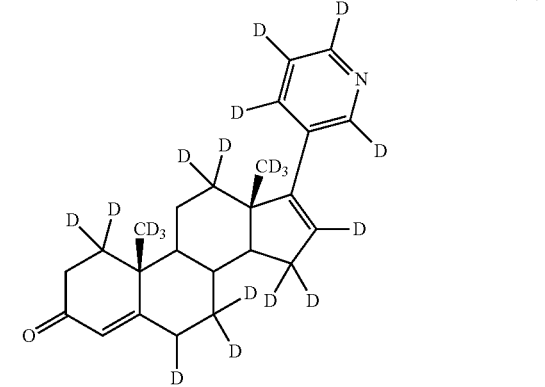
Formula (64)

-continued

Formula (65)

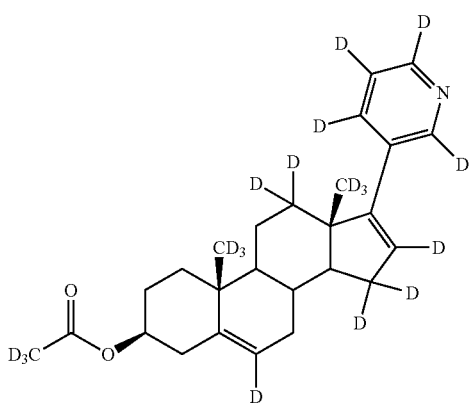

Formula (66)

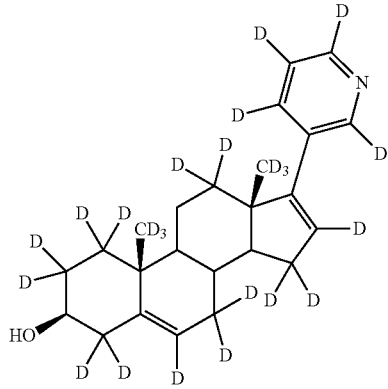

Formula (67)

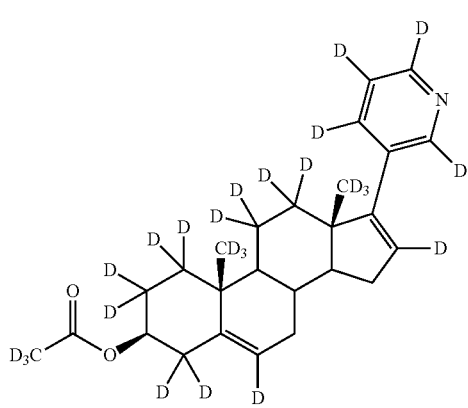

Formula (68)

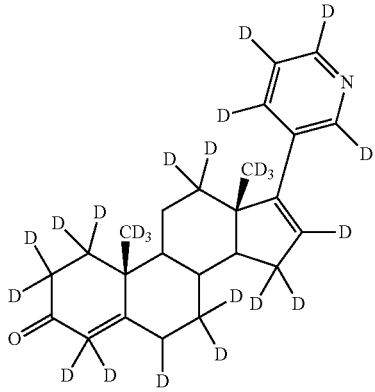

-continued

Formula (69)

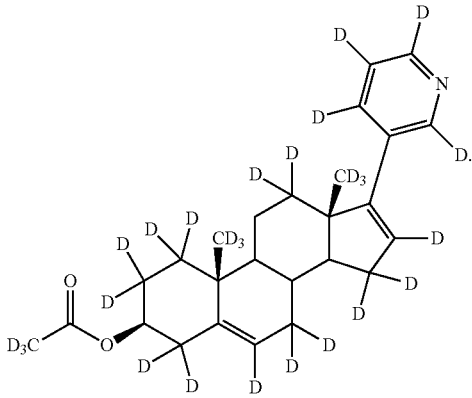

Among the above compounds, Formula (12), Formula (13), Formula (14), Formula (48), Formula (52), Formula (56), Formula (60), Formula (64), and Formula (68) are active metabolites of the compound of formula (I).

In another embodiment, the compound does not include non-deuterated compounds.

Also disclosed herein is a pharmaceutical composition comprising a pharmaceutically acceptable carrier and any one of the compound of Formula (I), or a crystal form, pharmaceutically acceptable salt, hydrate or solvate thereof.

Also disclosed herein is a pharmaceutical composition comprising a compound of Formula I, or a pharmaceutically acceptable salt thereof, or a pharmaceutically acceptable salt of the compound, and a pharmaceutically acceptable carrier. The carrier is "acceptable" in the sense of being compatible with the other ingredients of the formulation and, in the case of a pharmaceutically acceptable carrier, not deleterious to the recipient thereof in amounts used in the drug.

Also disclosed herein is a method of treating a disease or disorder associated with CYP17 enzymatic activity, the method comprising administering to a mammalian patient a compound of Formula (I), or a pharmaceutically acceptable salt or prodrug thereof.

Also disclosed herein is a compound of Formula (I), or a pharmaceutically acceptable salt or prodrug thereof, for use in the treatment of CYP17-related conditions.

The compound of Formula (I) and the composition comprising the compound are inhibitors of CYP17 enzyme and can be used to treat, prevent or eliminate various CYP17-related conditions. Pharmaceutical compositions containing these compounds are useful for treating and preventing a disease or a disorder, or slowing the progression of the disease or the disorder in various therapeutic fields such as in cancer.

Within the scope of the present invention, the above technical features and the technical features specifically described in the following (such as the examples) can be combined with each other to constitute a new or preferred technical solution.

Those skilled in the art will recognize that the chemical reactions described herein can be used to suitably prepare many other compounds disclosed herein, and that other methods for preparing the compounds disclosed herein are considered to be within the scope of the disclosure. For example, the synthesis of those non-exemplary compounds disclosed herein can be successfully accomplished by a person skilled in the art by modifying methods, such as appropriate protection of active groups, by using known reagents other than those as described herein, or by making some regular modifications to reaction conditions. In addition, the reaction disclosed herein or known reaction conditions are also generally recognized as suitable for the preparation of other compounds disclosed herein.

DETAILED DESCRIPTION

The present inventors have found that the deuterated steroidal compounds and pharmaceutically acceptable salts thereof disclosed herein have equivalent or superior pharmacokinetic and/or pharmacodynamic properties compared to non-deuterated compounds. Therefore, they are suitable as compounds that inhibit the CYP17 enzyme and are therefore more suitable for the preparation of a medication for the treatment of cancer and CYP17-related diseases. Based on this, the present disclosure was provided.

As used herein, "deuterated" means that one or more hydrogen(s) in a compound or group are substituted by deuterium(s). The deuterated can be mono-substituted, di-substituted, poly-substituted or fully substituted. The terms "substituted with one or more deuteriums" and "substituted by one or more deuteriums" are used interchangeably.

As used herein, "non-deuterated compound" refers to a compound containing deuterium in a ratio that is no more than the natural content of deuterium isotope (0.015%).

In another embodiment, the content of deuterium isotope at a deuterated position is greater than the natural content of deuterium isotope (0.015%), preferably greater than 50%, more preferably greater than 75%, more preferably greater than 95%, more preferably greater than 97%, more preferably greater than 99% and more preferably greater than 99.5%.

Specifically, in the present disclosure, the content of deuterium isotope in each deuterated position of $R^{1a}$, $R^{1b}$, $R^{1c}$, $R^{1d}$, $R^2$, $R^3$, $R^4$, $R^5$, $R^6$, $R^7$, $R^8$, $R^9$, $R^{10}$, $R^{11}$ and $R^{12}$ is at least 5%, preferably greater than 10%, more preferably more than 15%, still more preferably more than 20%, still more preferably more than 25%, still more preferably more than 30%, still more preferably more than 35%, still more preferably more than 40%, still more preferably more than 45%, still more preferably more than 50%, still more preferably more than 55%, still more preferably more than 60%, still more preferably more than 65%, still more preferably more than 70%, still more preferably more than 75%, still more preferably more than 80%, still more preferably more than 85%, still more preferably more than 90%, still more preferably more than 95%, and still more preferably more than 99%.

As used herein, the term "compounds disclosed herein" refers to compounds represented by Formula (I). The term also includes various crystal forms, pharmaceutically acceptable salts, prodrugs, metabolites, solvates, tautomers and stereoisomers of the compounds of Formula (I), including mixtures of these compounds in all ratios.

The phrase "pharmaceutically acceptable" as used herein refers to those compounds, materials, compositions, and/or dosage forms that are, within the scope of sound medical judgment, suitable for use in contact with human and animal tissues without causing excessive toxicity, irritation, allergies or other problems or complications, which are commensurate with a reasonable benefit/risk ratio.

As used herein, "a pharmaceutically acceptable salt" refers to derivatives of the described compounds wherein the parent compound is modified by the preparation of an acid or base salt thereof. Examples of pharmaceutically acceptable salts include, but are not limited to, mineral or organic acid salts of basic residues such as amines; and alkali or organic salts of acidic residues such as carboxylic acids. Pharmaceutical salts include conventional non-toxic salts or quaternary ammonium salts of the parent compound formed, for example, from non-toxic inorganic or organic acids. The pharmaceutically acceptable salts disclosed herein can be synthesized from the parent compound containing a basic or acidic moiety by conventional chemical methods. In general, the above salts may be prepared by reacting these compounds in free acid or base form with a stoichiometric amount of the appropriate base or acid in water or an organic solvent or a mixture of the two; typically, nonaqueous media such as diethyl ether, ethyl acetate, ethanol, isopropanol or acetonitrile are preferred. Suitable salts are found in Remington's Pharmaceutical Sciences, 17th Edition, Mack Publishing Company, Easton, Pa., p. 1418 (1985), the disclosure of which is incorporated herein by reference.

For example, a salt of a compound of Formula (I) may be formed by reacting a compound of Formula (I) with, for example, an equal amount of an acid or base in a medium that allows the newly formed salt to precipitate, for example, or be isolated by lyophilization. Exemplary acid salts of compounds of Formula (I) that may be formed with inorganic and/or organic acids include, but are not limited to, for example, acetates, ascorbates, benzoates, benzenesulfonates, hydrogensulfates, hydrogen tartrates, acidic citrates, citrates, esylates, formates, fumarates, gentisates, gluconates, glucarate, glutamates, hydrochlorides, hydrobromide, hydroiodide, isonicotinate, maleate, methanesulfonate, methanesulfonate, nitrate, pantothenate, phosphate, acidic phosphate, saccharate, salicylate, succinates, acid salts, tartrates, p-toluenesulfonates, trifluoroacetates, lactates, and pamoates (i.e., 1,1'-methylene-bis(2-hydroxy-naphthalene-3-carboxylic acid salt)). The above salts can be formed according to methods known to those skilled in the art.

Exemplary base salts of compounds of Formula (I) that may be formed with inorganic bases and/or organic bases include, but are not limited to, for example, ammonium salts; alkali metal salts such as sodium, lithium, and potassium salts; and alkaline earth metal salts such as calcium salts and magnesium salts; salts with organic bases such as benzathine, dicyclohexylamine, 2-amino-2-(hydroxymethyl)propane-1,3-diol (trihydroxymethyl amino-methane), hydrabamines (such as N,N-di-(dehydro-rosinyl)ethylenediamine), N-methyl-D-glucosamine, N-methyl-D-imidazole diamide and tert-butylamine; salts formed with amino acids such as arginine and lysine; and salts formed by quaternization of basic nitrogen-containing groups by the use of, for example, lower alkyl halides (e.g. methyl chloride, methyl bromide, methyl iodide, ethyl chloride, ethyl bromide, ethyl iodide, propyl chloride, propyl bromide, propyl iodide, butyl chloride, butyl bromide and butyl iodide), dialkyl sulfates (such as dimethyl sulfate, diethyl sulfate, dibutyl sulfate, and diamyl sulfate), long-chain halides (such as decyl chloride, decyl bromide, decyl iodide, lauryl chloride, lauryl bromide, lauryl iodide, myristyl chloride, myristyl bromide, myristyl iodide, stearyl chloride, stearyl bromide and stearyl iodide), and aralkyl halides (e.g. benzyl bromide and phenethyl bromide). The above salts can be formed according to methods known to those skilled in the art.

The term "solvate" refers to a complex in which a compound disclosed herein coordinates with a solvent molecule in a particular ratio. "Hydrate" refers to a complex formed by coordination of a compound disclosed herein with water.

In addition, the compounds disclosed herein also include prodrugs of steroidal compounds represented by Formula (I). The term "prodrug" includes a class of compounds or a salt or solution consisting of a compound of Formula (I), which may be biologically active or inactive itself, and when administered by an appropriate method, is metabolized or chemically reacted in the human body into the compound of Formula (I). Prodrugs include, but are not limited to, carboxylates, carbonates, phosphates, nitrates, sulfates, sulfone esters, sulfoxide esters, amino compounds, carbamates, azo compounds, phosphoramide, glucoside, ether, acetal of the compounds and the like.

The preferred prodrug compound is the acetate ester of the compound.

A "therapeutically effective amount" is meant to include the individual amounts of a compound disclosed herein or the combined amounts of the claimed compounds, or the combined amounts of a compound disclosed herein and other active ingredients that are effective as CYP17 enzyme antagonists or effective in the treatment of cancer.

As used herein, "treating" or "treatment" includes the treatment of disease states in mammals, particularly humans, and includes: (a) preventing the occurrence of said disease state in a mammal, particularly when the mammal is predisposed to the disease state but has not yet been diagnosed with the disease state; (b) inhibiting the disease state, i.e., preventing its development; and/or (c) relieving the disease state, i.e., making the disease state subside.

The compounds disclosed herein may contain one or more additional asymmetric carbon atoms and therefore may exist in two or more stereoisomeric forms. The present disclosure includes all possible single stereoisomers, their single tautomeric forms, and mixtures thereof. Diastereomers can be separated by conventional techniques, for example, by fractional crystallization, chromatography, or HPLC on mixtures of stereoisomers of a compound disclosed herein or a suitable salt or derivative thereof. The single enantiomers of the compounds may also be prepared from the corresponding optically pure intermediates or prepared by the resolution of the corresponding racemates using suitable chiral supports (such as by HPLC) or when appropriate, the fractional crystallization of diastereomeric salts which are prepared by reacting the corresponding racemate with a suitable optically active acid or base. All stereoisomers (in mixture or in pure or substantially pure form) of the compounds disclosed herein are included in the present disclosure.

The compounds disclosed herein are intended to include all isotopes of atoms occurring in the compounds. Isotopes include those atoms having the same atomic number but different atomic mass. As a general example but not limited thereto, isotopes of hydrogen include deuterium and tritium. Isotopes of carbon include $^{13}C$ and $^{14}C$. Isotopically-labeled compounds disclosed herein can generally be prepared by conventional techniques known to those skilled in the art or by methods similar to those described herein using isotopically-labeled appropriate reagents in place of unlabeled reagents which are used otherwise. Examples of isotopes that can be used in compounds disclosed herein include hydrogen, carbon, nitrogen, oxygen, phosphorus, sulfur, fluorine, and chlorine isotopes, such as $^{2}H$, $^{3}H$, $^{13}C$, $^{14}C$, $^{15}N$, $^{17}O$, $^{18}O$, $^{31}P$, $^{32}P$, $^{35}S$, $^{18}F$, and $^{36}Cl$, respectively. Compounds, or enantiomers, diastereomers, isomers, or pharmaceutically acceptable salts or solvates disclosed herein, wherein the above isotopes or other isotope atoms, are contained are within the scope of the present disclosure. Certain isotopically labeled compounds disclosed herein, such as the radioisotopes of $^{3}H$ and $^{14}C$, are also among them and are useful in the tissue distribution experiments of drugs and substrates. Tritium, i.e., $^{3}H$ and carbon-14, i.e., $^{14}C$, are easier to prepare and detect and are the first choice for isotopes. Isotopically-labeled compounds can be prepared using the schemes shown in the Examples by conventional methods by replacing the non-isotopic reagents with readily available isotopically labeled reagents.

The disclosure also includes a pharmaceutical composition comprising a compound of Formula (I) or a pharmaceutically acceptable salt thereof and one or more non-toxic pharmaceutically acceptable carriers and/or diluents and/or excipients (in this application collectively referred to as "carrier" material) and optionally other active ingredients. The compound of Formula (I) may be administered by any suitable route, preferably in the form of a pharmaceutical composition suitable for the above-described route, and in a dose effective for the treatment desired. For example, the compounds and compositions disclosed herein may be administered orally, mucosally, or parenterally (including intravascular, intravenous, intraperitoneal, subcutaneous, intramuscular, intrasternally and infusion techniques) in dosage unit Formulations containing conventional pharmaceutical carriers, adjuvants, and vehicles. For example, the pharmaceutical carrier may contain mannitol or a mixture of lactose and microcrystalline cellulose. The mixture may contain other components such as a lubricant (such as magnesium stearate) and a disintegrant (such as crospovidone). The carrier mixture can be filled into gelatin capsules or compressed into tablets.

The pharmaceutically active compounds disclosed herein may be processed according to conventional pharmaceutical methods to prepare medicaments for administration to patients, including humans and other mammals.

For oral administration, the pharmaceutical composition may be in the form of, for example, a tablet, capsule, suspension, or liquid Formulation. The pharmaceutical compositions are preferably prepared in dosage unit form containing a specific amount of the active ingredient. Examples of such dosage units are tablets or capsules.

The amount of compound administered and the dosing regimen used to treat conditions with the compounds and/or compositions disclosed herein will depend on a variety of factors including the subject's age, weight, sex and medical condition, type of disease, severity of the disease, the route and frequency of administration and the specific compound used. Thus, the dosing regimen can vary widely, but can be routinely determined using standard methods.

For therapeutic purposes, the active compounds of the present disclosure are usually combined with one or more excipients suitable for the intended route of administration. If administered orally, the compound may be mixed with lactose, sucrose, starch powders, cellulose alkanoates, cellulose alkyl esters, talc, stearic acid, magnesium stearate, magnesium oxide, sodium and calcium salts of phosphoric and sulfuric acids, gelatin, gum arabic, sodium alginate, polyvinyl alcohol and/or polyvinyl pyrrolidone, and then tableted or encapsulated for ease of administration. The capsules or tablets described above may include a controlled release formulation which may be provided as a dispersion of the active compound in hydroxypropylmethylcellulose.

The oil phase of the emulsion containing the compound of Formula (I) can be constituted from known ingredients in a known manner. Although the phase may comprise only an emulsifier, it may comprise a mixture of at least one emulsifier with a fat or an oil or with a fat and an oil. Preferably, the hydrophilic emulsifier and the lipophilic emulsifier as a stabilizer are contained together. It is also preferred that both oil and fat are included. In addition, emulsifiers (with or without stabilizers) constitute so-called emulsifying waxes and together with oils and fats form the so-called emulsifying ointment bases which form the oily dispersed phase of the creams. The emulsifier and emulsion stabilizers suitable for use in the Formulations of the disclosure include Tween 60, Span 80, cetearyl alcohol, myristyl alcohol, glyceride monostearate, sodium lauryl sulfate or glyceryl distearate. These materials are used alone or with wax or other materials known in the art.

The pharmaceutical composition may undergo conventional pharmaceutical operations such as sterilization and/or may contain conventional excipients such as preservatives, stabilizers, wetting agents, emulsifiers, buffers, and the like. Tablets and pills can also be prepared with enteric coatings. The composition may also contain excipients such as wetting agents, sweeteners, flavoring agents and fragrances.

The pharmaceutical composition disclosed herein comprises a compound of Formula (I) or a pharmaceutically acceptable salt thereof and optionally other substances selected from any pharmaceutically acceptable carriers, excipients and vehicles. Alternative compositions disclosed herein comprise a compound of Formula (I) or a pharmaceutically acceptable salt thereof as described herein and a pharmaceutically acceptable carrier, adjuvant or vehicle.

Compounds of Formula (I) are useful for treating cancer, such as cancers that depend on androgen receptor signaling. These compounds inhibit the activity of the CYP17 enzyme involved in androgen biosynthesis. Blocking of the enzyme can inhibit the androgens production in gonad, adrenal gland, and tumor, and provides a new option for the treatment of patients with cancers that rely on androgen receptor signaling such as prostate cancer and estrogen receptor-positive breast cancer. Thus, the treatment comprises administering to the patient a compound of Formula (I) or a pharmaceutically acceptable salt thereof.

In one embodiment, a method for treating cancer is provided, said method comprising administering to a mammal in need thereof a compound of Formula (I). The method of this embodiment can be used to treat a variety of cancers, including but not limited to bladder cancer, breast cancer, colorectal cancer, gastric cancer, head and neck cancer, kidney cancer, liver cancer, lung cancer, ovarian cancer, pancreatic/gallbladder cancer, prostate cancer, thyroid cancer, osteocarcinoma, rhabdomyosarcoma, malignant fibrous histiocytoma (MFH), fibrosarcoma, glioblastoma/astrocytoma, melanoma, and mesothelioma.

Preferably, the method of this embodiment is used to treat a variety of prostate cancers.

The amount of the compound of Formula (I) administered and the dosing regimen used to treat a particular cancer depend on a variety of factors, including the subject's age, weight, sex and medical state, type of disease, severity of the disease, the route and frequency of administration and the specific compound used. Thus, the dosing regimen can vary widely, but can be routinely determined using standard methods. A daily dose of about 0.01 to 1500 mg/kg body weight, preferably about 0.5 to about 50 mg/kg body weight and most preferably about 0.1 to 20 mg/kg body weight may be suitable. The daily dose may be administered in 1-4 doses per day.

When treating cancer, combinations of chemotherapeutic agents and/or other treatments (e.g., radiation therapy) are often advantageous. The second (or third) agent may have the same or different mechanism of action as the primary therapeutic agent. The use of cytotoxic drug combinations may be particularly useful where two or more drugs that act in different ways or on different phases of cell cycles are administered, and/or where two or more drugs have overlapping toxicities or side effects, and/or the drugs that are combined when treating a particular disease state exhibited by the patient each have a significant effect.

Thus, compounds of Formula (I) may be administered in combination with other anti-cancer treatments for the treatment of cancer or other proliferative diseases. The present disclosure further includes the use of a compound of Formula (I) in the manufacture of a medicament for the treatment of cancer, and/or a package comprising a compound of Formula (I) disclosed herein and instructions, wherein said compound is used in combination with other anticancer agents or cytotoxic agents and used in the treatment of cancer. The disclosure further comprises a combination of a compound of Formula (I) and one or more other pharmaceutical agents in the form of a kit, for example they are packaged together or placed in separate packages for sale together as a kit or they are packaged together for Formulation.

Other anti-cancer agents may be selected from one or more of the following: alkylating agents (including nitrogen mustards, alkyl sulfonates, nitrosoureas, ethylenimine derivatives and triazene); anti-angiogenic agents (includes matrix metalloproteinase inhibitors); antimetabolites (including adenosine deaminase inhibitors, folate antagonists, purine analogs, and pyrimidine analogs); antibiotics or antibodies (including monoclonal antibodies, CTLA-4 antibodies, anthracycline antibiotics); aromatase inhibitors; cell cycle response regulators; enzymes; farnesyl-protein transferase inhibitors; hormonal and antihormonal agents and steroids (including synthetic analogs, glucocorticoids, estrogens/antiestrogens (e.g., SERMs), androgens/antiandrogens, progestogens, progesterone receptor agonists, and luteinizing hormone release agonists and antagonists); insulin-like growth factor/insulin-like growth factor receptor systemic modulators; integrin signalling inhibitors; kinase inhibitors (including multi-kinase inhibitors and/or Src kinases or Src/abl inhibitors), cyclin-dependent kinase (CDK) inhibitors, panHer, Her-1 and Her-2 antibody, VEGF inhibitors (including anti-VEGF antibodies), EGFR inhibitors, mitogen-activated protein [MAP] inhibitors, MEK inhibitors, Aurora kinase inhibitors, PDGF inhibitors and other tyrosine kinase inhibitors or serine/threonine kinase inhibitors; microtubule interferers, such as ecteinases or their analogs and derivatives; microtubule stabilisers such as taxanes and naturally occurring epothilone and their synthetic and semi-synthetic analogs; microtubule binding and destabilizing agents (including vinca alkaloids); topoisomerase inhibitors; prenyl-protein transferase inhibitors; platinum coordination complexes; signal transduction inhibitors; and other agents used as anti-cancer and cytotoxic agents, such as biological response modifiers, growth factors and immunomodulators.

Preparation

The method for preparing the compounds of the Formula (I) disclosed herein will be more specifically described below, but these specific methods do not impose any limitations on the present disclosure. The compounds disclosed herein can also be conveniently prepared by combining various synthetic methods described in this specification or known in the art, and such combinations can be easily performed by those skilled in the art to which the present disclosure pertains.

The following general preparative routes can be used to synthesize the compounds of Formula (I) disclosed herein:

Synthetic Route

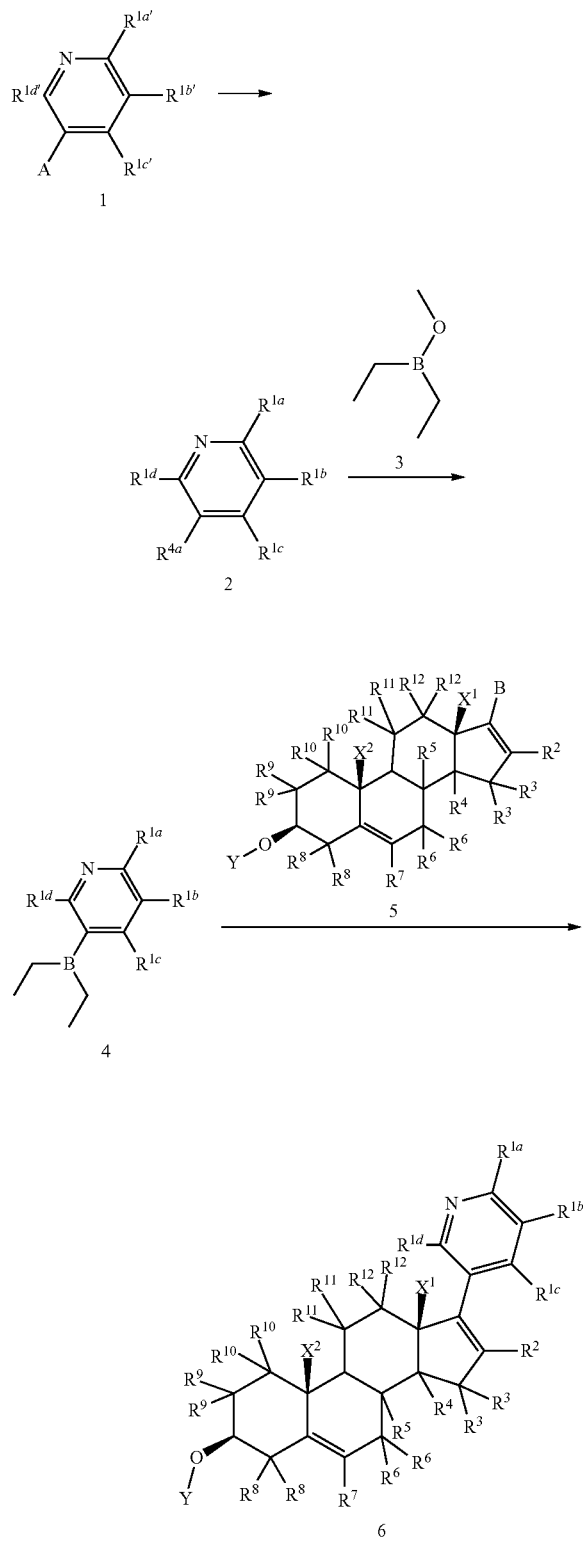

wherein: A, B, $R^{1a'}$, $R^{1b'}$, $R^{1c'}$, and $R^{1d'}$ are selected from F, Cl, Br, and I, wherein A is preferably Br, B, $R^{1a'}$, $R^{1b'}$, $R^{1c'}$, and $R^{1d'}$ are preferably I, the definitions of $R^{1a'}$, $R^{1b'}$, $R^{1c'}$, and $R^{1d'}$, $R^2$, $R^3$, $R^4$, $R^5$, $R^6$, $R^7$, $R^8$, $R^9$, $R^{10}$, $R^{11}$, $R^{12}$, $X^1$, $X^2$, and Y are as described above.

The solvent used in the above reaction is selected from dichloromethane, dichloroethane, ethyl acetate, methyl acetate, isopropyl acetate, n-hexane, n-heptane, petroleum ether, n-butanol, ethanol, isobutanol, tert-butyl alcohol, isopropanol, n-propanol, n-pentanol, isoamyl alcohol, acetone, acetonitrile, n-hexane, toluene, tetrahydrofuran, 2-methyltetrahydrofuran, 1,4-dioxane, ethylene glycol monomethyl ether, ethylene glycol dimethyl ether, N,N-dimethylformamide, N,N-dimethylacetamide, dimethyl sulfoxide and the like.

The base used in the above reaction is selected from potassium carbonate, sodium carbonate, sodium bicarbonate, cesium carbonate, sodium hydroxide, potassium hydroxide, lithium hydroxide, triethylamine, diisopropylethylamine, 4-N,N-dimethylpyridine, pyridine and the like.

The above reaction temperature is −30° C. to 200° C., more preferably −10° C. to 100° C.

The above reaction time is 0-48 h, more preferably 0-24 h, and more preferably 0-6 h.

Pharmaceutical Composition and Method of Administration

The compounds disclosed herein have a series of advantages over non-deuterated compounds known in the art.

The main advantages of the present disclosure include: (1) The compounds disclosed herein have excellent inhibitory properties against the CYP17 enzyme; (2) the deuteration technology changes the metabolism of the compound in the organism, so that the compound has better pharmacokinetic parameters characteristics. In this case, the dosage can be changed and a long-acting formulation can be formed to improve the applicability; (3) replacement of hydrogen atom in compounds with deuterium can increase the drug concentration of the compound in the animal body due to its deuterium isotope effect, so as to improve the drug efficacy; (4) replacement of hydrogen atom in compounds with deuterium may increase the safety of the compound due to the inhibition of certain metabolites.

The following further describes the present disclosure in combination with specific examples. It should be understood that these examples are only for illustrating the present disclosure and are not intended to limit the scope of the present disclosure. The experimental methods that do not specify specific conditions in the following examples are generally based on conventional conditions or according to manufacturer's recommended conditions. Parts and percentages are parts by weight and percentages by weight unless otherwise indicated.

Example 1. Synthesis of (3β)-17-(3-pyridyl-6-d) androst-5,16-dienol (Compound 12)

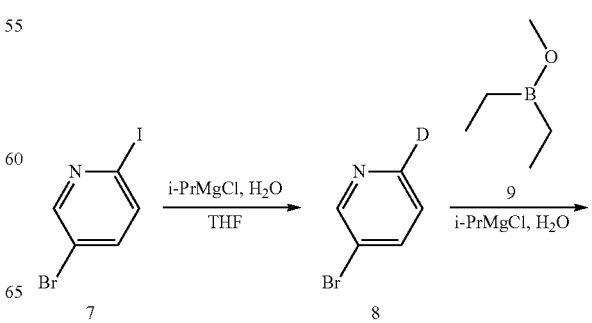

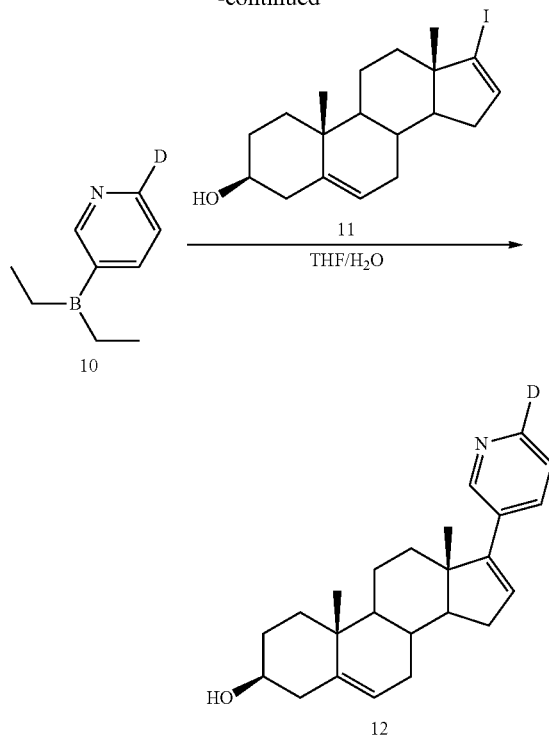

Step 1: Synthesis of 3-bromo-6-d-pyridine (Compound 8)

Under an ice bath, isopropylmagnesium chloride (2M/THF, 6.16 mL, 12.31 mmol) was slowly added dropwise to a solution of 5-bromo-2-iodopyridine (3.4 g, 11.72 mmol) in tetrahydrofuran (12 mL). After the completion of the addition, the mixture was reacted at 0° C. for 1 h. And then deuterated methanol-d4 (2.0 mL) was slowly added dropwise to the reaction solution. The reaction system was warmed to room temperature and stirred for 0.5 h. The reaction was quenched with 30 mL of saturated aqueous ammonium chloride, and extracted with dichloromethane (30 mL×3). The organic layer was dried over anhydrous magnesium sulfate, and concentrated under reduced pressure. The concentrate was purified by column chromatography (eluent: PE/EtOAc (v/v)=15/1), obtaining 600 mg of a pale yellow liquid. Yield: 37.7%. $^1$H NMR (300 MHz, CDCl$_3$) (δ/ppm) 8.70 (d, J=2.0 Hz, 1H), 7.83 (dd, J=8.2, 2.4 Hz, 1H), 7.21 (d, J=8.2 Hz, 1H).

Step 2: Synthesis of 3-(diethylboryl)-6-d-pyridine (Compound 10)

Under an ice bath, isopropylmagnesium chloride (2M/THF, 2.1 mL, 4.20 mmol) was slowly added dropwise to a solution of 3-bromo-6-d-pyridine (556 mg, 3.5 mmol) in tetrahydrofuran (5 mL). After the completion of the addition, the mixture was reacted at 0° C. for 1.5 h. And then diethyl methoxyborane (1 M/THF, 4.2 mL, 4.2 mmol) was slowly added dropwise to the reaction solution. The reaction system was warmed to room temperature and stirred for 1 h. The reaction was quenched with 30 mL of saturated aqueous ammonium chloride, and extracted with dichloromethane (30 mL×3). The organic layer was dried over anhydrous magnesium sulfate, and concentrated under reduced pressure, and the concentrate was purified by column chromatography (eluent: PE/EtOAc (v/v)=1/0), obtaining 300 mg of a white solid, yield: 48.3%. $^1$H NMR (300 MHz, CDCl$_3$) (δ/ppm) 7.74 (dd, J=7.5, 1.3 Hz, 1H), 7.59 (s, 1H), 7.26 (d, J=7.5 Hz, 1H), 0.76-0.61 (m, 4H), 0.48 (t, J=7.4 Hz, 6H).

Step 3: Synthesis of (3β)-17-(3-pyridyl-6-d)androst-5,16-diene-ol

At room temperature, under nitrogen protection, a mixed solution of tetrahydrofuran (6 mL) and water (2 mL) was added to a mixture of (3β)-17-iodoandrost-5,16-diene-ol (200 mg, 0.50 mmol), 3-(diethylboryl)-6-d-pyridine (88 mg, 0.60 mmol), bis(triphenylphosphine)palladium (II) chloride (PdCl$_2$(PPh$_3$)$_2$) (20 mg, 0.04 mmol), and sodium carbonate (210 mg, 2.00 mmol). The reaction solution was kept at 80° C. overnight (16 hrs). After cooled to room temperature, the reaction was quenched with water (25 mL), and filtered through celite, and the filtrate was extracted with ethyl acetate (30 mL×3). The organic layers were combined, washed with brine (30 mL), dried over anhydrous sodium sulfate, and concentrated under reduced pressure. The concentrate was purified by column chromatography (eluent: PE/EtOAc (v/v)=1.5/1) to give 100 mg of a white solid, yield: 57.1%, purity: 97.21%, LC-MS (APCI): m/z=351.10 (MO. $^1$H NMR (300 MHz, MeOD-d) (δ/ppm) 8.54 (d, J=1.5 Hz, 1H), 7.86 (dd, J=8.0, 2.3 Hz, 1H), 7.39 (dd, J=8.0, 0.7 Hz, 1H), 6.11 (dd, J=3.2, 1.8 Hz, 1H), 5.41 (d, J=5.1 Hz, 1H), 3.48-3.37 (m, 1H), 2.36-2.23 (m, 3H), 2.16-2.04 (m, 3H), 1.95-1.79 (m, 3H), 1.77-1.61 (m, 4H), 1.58-1.45 (m, 2H), 1.14-1.05 (m, 8H).

Example 2 Synthesis of (3β)-17-(3-pyridyl-5-d)androst-5,16-dienol (Compound 18)

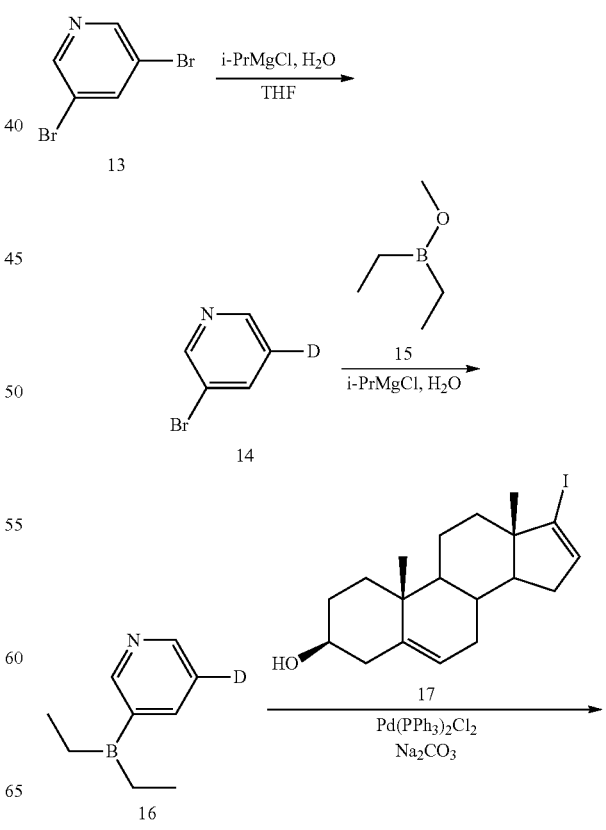

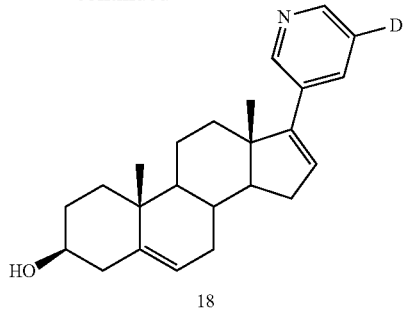

Step 1: Synthesis of 3-bromo-5-d-pyridine (Compound 14)

Under an ice bath, isopropylmagnesium chloride (2M/THF, 7.5 mL, 15.00 mmol) was slowly added dropwise to a solution of 3,5-dibromopyridine (3.55 g, 15.00 mmol) in tetrahydrofuran (15 mL). After the completion of the addition, the mixture was reacted at 0° C. for 1.5 h. The heavy water (2.0 mL) was slowly added dropwise to the reaction solution. The reaction system was warmed to room temperature and stirred overnight at room temperature. The reaction was quenched with 30 mL of saturated aqueous ammonium chloride, and extracted with dichloromethane (60 mL×3). The organic layer was dried over anhydrous magnesium sulfate, and concentrated under reduced pressure, and the concentrate was purified by column chromatography (eluent: PE/EtOAc (v/v)=15/1), obtaining 1.30 g of a pale yellow liquid, yield: 54.8%. $^1$H NMR (300 MHz, CDCl$_3$) (δ/ppm) 8.70 (d, J=2.4 Hz, 1H), 8.54 (s, 1H), 7.83 (dd, J=2.2, 1.0 Hz, 1H).

Step 2: Synthesis of 3-(diethylboryl)-5-d-pyridine (Compound 16)

Under an ice bath, isopropylmagnesium chloride (2M/THF, 4.83 mL, 9.66 mmol) was slowly added dropwise to a solution of 3-bromo-5-d-pyridine (1.28 g, 8.05 mmol) in tetrahydrofuran (15 mL). After the completion of the addition, the mixture was reacted at 0° C. for 1.5 h. The diethyl methoxyborane (1 M/THF, 9.7 mL, 9.66 mmol) was slowly added dropwise to the reaction solution. The reaction system was warmed to room temperature and stirred for 1 h at room temperature. The reaction was quenched with 30 mL of saturated aqueous ammonium chloride, and extracted with dichloromethane (30 mL×3). The organic layer was dried over anhydrous magnesium sulfate, and concentrated under reduced pressure, and the concentrate was purified by column chromatography (eluent: PE/EtOAc (v/v)=1/0), obtaining 400 mg of a white solid, yield: 33.7%. $^1$H NMR (300 MHz, CDCl$_3$) (δ/ppm) 8.03 (s, 1H), 7.74 (s, 1H), 7.59 (s, 1H), 0.70 (m, 4H), 0.48 (t, J=7.4 Hz, 6H).

Step 3: Synthesis of (3β)-17-(3-pyridyl-5-d)androst-5,16-dienol (Compound 18)

At room temperature, under nitrogen protection, a mixed solution of tetrahydrofuran (6 mL) and water (2 mL) was added to a mixture of (3β)-17-iodoandrost-5,16-dienol (200 mg, 0.50 mmol), 3-(diethylboryl)-5-d-pyridine (88 mg, 0.60 mmol), bis(triphenylphosphine)palladium (II) chloride (PdCl$_2$(PPh$_3$)$_2$) (20 mg, 0.04 mmol), and sodium carbonate (210 mg, 2.00 mmol). The reaction solution was kept at 80° C. overnight (16 hrs). After cooled to room temperature, the reaction was quenched with water (25 mL), filtered through celite, and the filtrate was extracted with ethyl acetate (30 mL×3). The organic layers were combined, washed with brine (30 mL), dried over anhydrous sodium sulfate, and concentrated under reduced pressure. The concentrate was purified by column chromatography (eluent: PE/EtOAc (v/v)=1.5/1) to afford 90 mg of a white solid, yield: 57.39%, purity: 96.03%, LC-MS (APCI): m/z=351.1 (M+1), $^1$H NMR (300 MHz, MeOD-d) (δ/ppm) 8.55 (d, J=2.2 Hz, 1H), 8.40 (d, J=1.4 Hz, 1H), 7.86 (s, 1H), 6.11 (dd, J=3.1, 1.8 Hz, 1H), 5.41 (d, J=5.1 Hz, 1H), 3.50-3.36 (m, 1H), 2.37-2.22 (m, 3H), 2.15-2.05 (m, 3H), 1.94-1.79 (m, 3H), 1.76-1.60 (m, 4H), 1.58-1.44 (m, 2H), 1.18-1.03 (m, 8H).

Example 3 Synthesis of (3β)-17-(3-pyridyl-5-d) androst-5,16-dienyl Acetate (Compound 20)

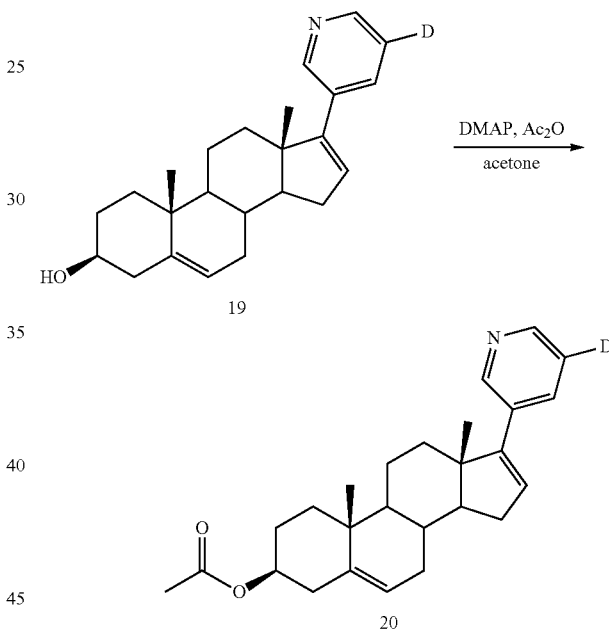

At room temperature, DMAP (4-dimethylaminopyridine) (4.00 mg, 0.02 mmol) was added to a solution of (3β)-17-(3-pyridyl-5-d)androst-5,16-dienol (45 mg, 0.13 mmol) and acetic anhydride (40 mg, 0.40 mmol) in acetone (3 mL). The reaction was stirred at 55° C.-65° C. for 2 h. The acetone was removed under reduced pressure and 15 mL of water was added to quench the reaction. The reaction was extracted with ethyl acetate (20 mL×3). The combined organic phases were washed with brine, dried over anhydrous sodium sulfate, and concentrated under reduced pressure, and the concentrate was purified by column chromatography (eluent: PE/EtOAc (v/v)=3/1) to give 30 mg of an off-white solid. Yield: 74.5%, purity: 96.31%, LC-MS (APCI): m/z=393.3 (M+1), $^1$H NMR (300 MHz, DMSO-d$_6$) (δ/ppm) 8.59 (s, 1H), 8.43 (s, 1H), 7.76 (s, 1H), 6.12 (s, 1H), 5.39 (d, J=4.3 Hz, 1H), 4.55-4.34 (m, 1H), 2.33-2.25 (m, 2H), 2.25-2.15 (m, 1H), 2.11-2.00 (m, 3H), 1.99 (s, 3H), 1.87-1.75 (m, 2H), 1.71-1.47 (m, 6H), 1.43-1.34 (m, 1H), 1.13-1.06 (m, 1H), 1.06-0.97 (m, 7H).

Example 4 Synthesis of (3β)-17-(3-pyridyl)androst-5,16-dienyl d3-acetate (Compound 23)

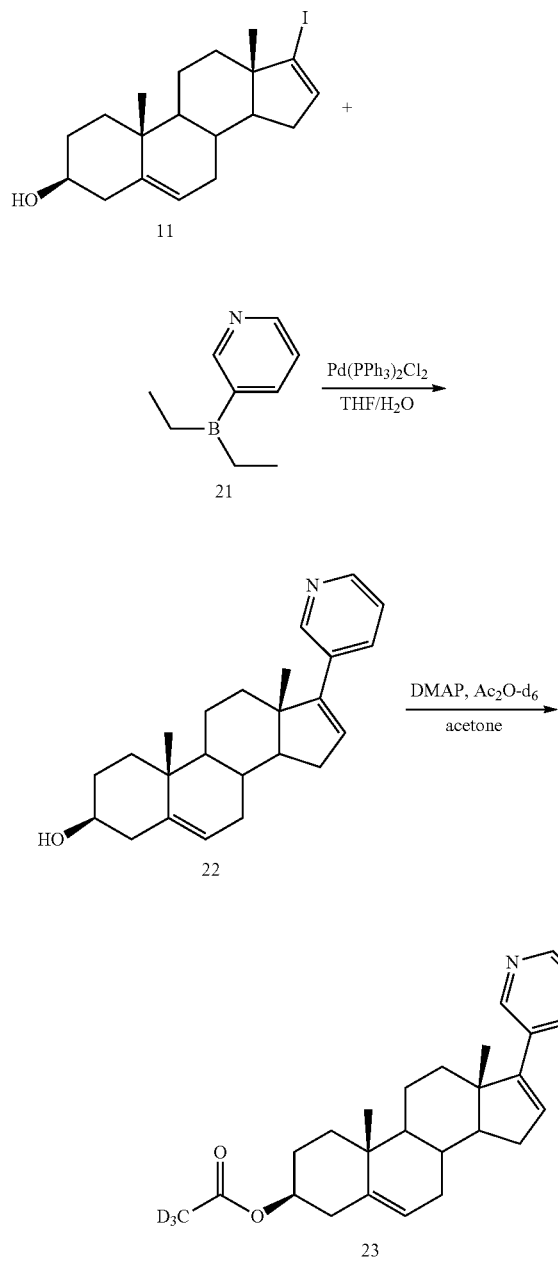

Step 1: Synthesis of (3β)-17-(3-pyridinyl)androst-5,16-dienol (Compound 22)

At room temperature, under nitrogen protection, a mixed solution of tetrahydrofuran (30 mL) and water (10 mL) was added to a mixture of 17-iodoandrost-5,16-diene-3β-alcohol (2.00 g, 5.02 mmol), 3-diethylboranylpyridine (900 mg, 6.02 mmol), bis(triphenylphosphine)palladium (II) chloride (180 mg, 0.26 mmol), and sodium carbonate (2.12 g, 20.08 mmol). The reaction solution was kept at 80° C. overnight (16 hrs). After cooled to room temperature, the reaction was quenched with water (25 mL), and filtered through celite, and the filtrate was extracted with ethyl acetate (60 mL×3). The organic layers were combined, washed with brine (60 mL), dried over anhydrous sodium sulfate and concentrated under reduced pressure, and the concentrate was purified by column chromatography (eluent: PE/EtOAc (v/v)=1/1) to give 1.25 g of a pale yellow solid, yield: 71.2%, purity: 96.25%, LC-MS (APCI): m/z=350.1 (M+1)⁺. ¹H NMR (300 MHz, MeOD-d₄) (δ/ppm) 8.54 (s, 1H), 8.40 (d, J=4.0 Hz, 1H), 7.86 (d, J=8.1 Hz, 1H), 7.39 (dd, J=7.8, 4.9 Hz, 1H), 6.10 (s, 1H), 5.41 (d, J=5.0 Hz, 1H), 3.49-3.37 (m, 1H), 2.36-2.21 (m, 3H), 2.17-2.00 (m, 3H), 1.95-1.78 (m, 3H), 1.76-1.62 (m, 4H), 1.56-1.44 (m, 2H), 1.15-1.06 (m, 8H).

Step 2: Synthesis of (3β)-17-(3-pyridyl)androst-5,16-dienyl d3-acetate (Compound 23)

At room temperature, DMAP (4-dimethylaminopyridine) (5.00 mg, 0.04 mmol) was added to a solution of 3β-17-(3-pyridyl)androst-5,16-dienol (70 mg, 0.20 mmol) and deuterated acetic anhydride-d6 (61 mg, 0.60 mmol) in acetone (5 mL). The reaction solution was stirred at 55° C.-65° C. for 2 hours. The acetone was removed under reduced pressure and 15 mL of water was added to quench the reaction. The reaction was extracted with ethyl acetate (20 mL×3). The combined organic phases were washed with brine and dried over anhydrous sodium sulfate. The organic layer was concentrated under reduced pressure and the concentrate was purified by column chromatography (eluent: PE/EtOAc (v/v)=3/1) to give 65 mg of an off-white solid. Yield: 82.4%, purity: 97.46%. LC-MS (APCI): m/z=395.3 (M+1). ¹H NMR (300 MHz, DMSO-d₆) (δ/ppm) 8.59 (d, J=1.7 Hz, 1H), 8.44 (dd, J=4.7, 1.5 Hz, 1H), 7.81-7.72 (m, 1H), 7.34 (dd, J=7.9, 4.8 Hz, 1H), 6.12 (d, J=1.3 Hz, 1H), 5.39 (d, J=4.4 Hz, 1H), 4.57-4.36 (m, 1H), 2.34-2.26 (m, 2H), 2.26-2.16 (m, 1H), 2.10-1.97 (m, 3H), 1.88-1.74 (m, 2H), 1.72-1.46 (m, 6H), 1.46-1.32 (m, 1H), 1.15-1.00 (m, 8H).

Example 5 Synthesis of (3β)-17-(3-pyridyl-6-d)androst-5,16-dienyl Acetate (Compound 25)

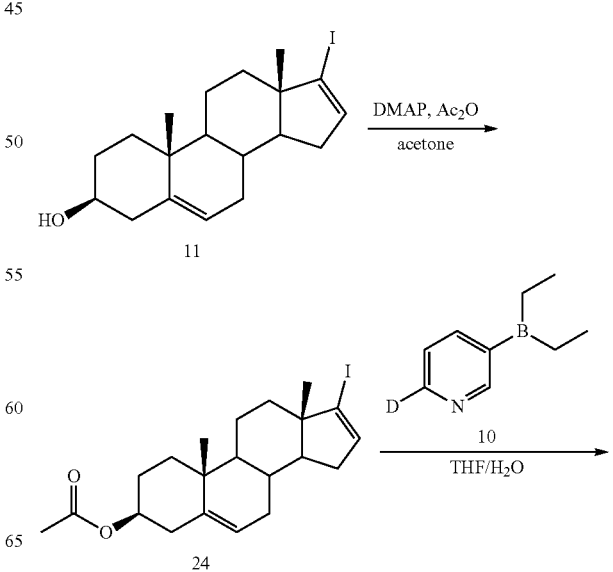

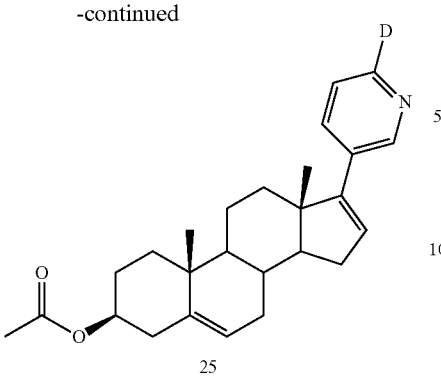

Step 1: Synthesis of (3β)-17-iodoandrost-5,16-dienyl Acetate (Compound 24)

At room temperature, DMAP (4-dimethylaminopyridine) (107 mg, 0.88 mmol) was added to a solution of (3β)-17-iodoandrost-5,16-dienol (3.5 g, 8.78 mmol) and acetic anhydride (2.69 g, 26.34 mmol) in acetone (15 mL). The reaction solution was stirred at 55° C.–65° C. for 2 hours. The acetone was removed under reduced pressure. The reaction was quenched by the addition of 30 mL of water and extracted with ethyl acetate (30 mL×3). The combined organic phases were washed with brine, dried over anhydrous sodium sulfate, concentrated under reduced pressure, and the concentrate was purified by column chromatography (eluent: PE/EtOAc (v/v)=3/1) to give 1.50 g of an off-white solid, yield: 38.8%.

Step 2: Synthesis of (3β)-17-(3-pyridyl-6-d)androst-5,16-dienyl Acetate (Compound 25)

At room temperature, under nitrogen protection, a mixed solution of tetrahydrofuran (6 mL) and water (2 mL) was added to a mixture of 17-iodoandrost-5,16-diene-3β-yl acetate (160 mg, 0.36 mmol), 3-diethylboranylpyridine-6-d (54 mg, 0.36 mmol), bis(triphenylphosphine)palladium (II) chloride $PdCl_2(PPh_3)_2$ (15 mg, 0.02 mmol), and sodium carbonate (140 mg, 1.30 mmol). The reaction solution was reacted at 80° C. for 2 hours. After cooled to room temperature, the reaction was quenched with water (15 mL), filtered through celite, and the filtrate was extracted with ethyl acetate (25 mL×3). The organic layers were combined and the organic layer was washed with brine (30 mL) and dried over anhydrous sodium sulfate. The organic layer was concentrated under reduced pressure and purified by column chromatography (eluent: PE/EtOAc (v/v)=4/1) to give 36 mg of a white solid, yield: 25.5%, purity: 98.89%, LC-MS (APCI): m/z=393.3 (M+1)$^+$. $^1$H NMR (300 MHz, DMSO-$d_6$) (δ/ppm) 8.63 (s, 1H), 7.89 (dd, J=8.0, 1.9 Hz, 1H), 7.44 (d, J=8.0 Hz, 1H), 6.18 (s, 1H), 5.39 (d, J=4.1 Hz, 1H), 4.57-4.34 (m, 1H), 2.29 (d, J=7.8 Hz, 2H), 2.25-2.15 (m, 1H), 2.11-2.00 (m, 3H), 1.98 (s, 3H), 1.87-1.73 (m, 2H), 1.72-1.48 (m, 6H), 1.45-1.34 (m, 1H), 1.14-1.06 (m, 1H), 1.06-0.98 (m, 7H).

Example 6 Synthesis of (3β)-17-(3-pyridyl-6-d)androst-5,16-dienyl d3-acetate (Compound 27)

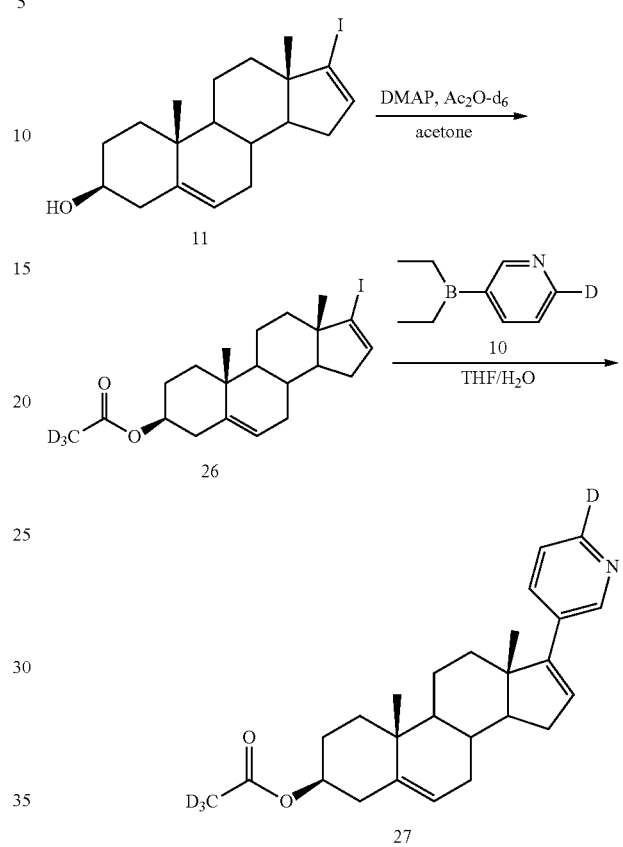

Step 1: Synthesis of (3β)-17-iodoandrost-5,16-dienyl d3-acetate (Compound 26)

At room temperature, DMAP (4-dimethylaminopyridine) (61 mg, 0.50 mmol) was added to a solution of (3β)-17-iodoandrost-5,16-dienol (2.00 g, 5.00 mmol) and deuterated acetic anhydride-d6 (1.50 g, 15.00 mmol) in acetone (15 mL). The reaction was stirred at 55-65° C. for 2 hours. The acetone was removed under reduced pressure. The reaction was quenched by the addition of 30 mL of water and extracted with ethyl acetate (30 mL×3). The combined organic phases were washed with brine and dried over anhydrous sodium sulfate. The organic layer was concentrated under reduced pressure, and the concentrate was purified by column chromatography (eluent: PE/EtOAc (v/v)=3/1) to give 1.80 g of a white solid. Yield: 81.23%. $^1$H NMR (300 MHz, CDCl$_3$) (δ/ppm) 6.14 (dd, J=3.1, 1.6 Hz, 1H), 5.39 (d, J=5.1 Hz, 1H), 4.61 (m, 1H), 2.34 (m, 2H), 2.16 (m, 1H), 1.74 (m, 12H), 1.21 (m, 2H), 1.06 (s, 3H), 0.76 (s, 3H).

Step 2: Synthesis of (3β)-17-(3-pyridyl-6-d)androst-5,16-dienyl d3-acetate (Compound 27)

At room temperature, under nitrogen protection, a mixed solution of tetrahydrofuran (6 mL) and water (2 mL) was added to a mixture of (3β)-17-iodoandrost-5,16-dienyl d3-acetate (160 mg, 0.36 mmol), 3-diethylboranyl-6-d-pyridine (54 mg, 0.36 mmol), bis(triphenylphosphine)palladium (II) chloride PdCl$_2$(PPh$_3$)$_2$ (15 mg, 0.02 mmol), and sodium carbonate (140 mg, 1.30 mmol). The reaction solution was reacted at 80° C. for 2 h. After cooled to room temperature, the reaction was quenched with water (15 mL), filtered through celite, and the filtrate was extracted with ethyl acetate (25 mL×3). The organic layers were combined and the organic layer was washed with brine (30 mL) and dried over anhydrous sodium sulfate. The organic layer was concentrated under reduced pressure and purified by column chromatography (eluent: PE/EtOAc (v/v)=4/1) to give 65 mg of a white solid, yield: 46.0%, purity: 99.82%, LC-MS (APCI): m/z=396.3 (M+1)$^+$. $^1$H NMR (300 MHz, DMSO-d$_6$) (δ/ppm) 8.60 (d, J=1.4 Hz, 1H), 7.80 (dd, J=8.0, 2.0 Hz, 1H), 7.36 (d, J=7.9 Hz, 1H), 6.13 (s, 1H), 5.38 (d, J=4.1 Hz, 1H), 4.55-4.34 (m, 1H), 2.28 (d, J=7.7 Hz, 2H), 2.24-2.13 (m, 1H), 2.09-1.94 (m, 3H), 1.86-1.73 (m, 2H), 1.70-1.46 (m, 6H), 1.44-1.32 (m, 1H), 1.22-1.07 (m, 1H), 1.06-0.98 (m, 7H).

Example 7 Synthesis of (3β)-17-(3-pyridyl-5-d) androst-5,16-dienyl d3-acetate (Compound 28)

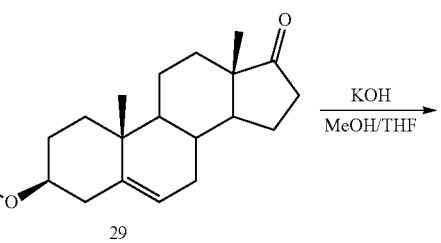

At room temperature, under nitrogen protection, a mixed solution of tetrahydrofuran (2.2 mL) and water (0.7 mL) was added to a mixture of (3β)-17-iodoandrost-5,16-dienyl d$_3$-acetate (Compound 26) (150 mg, 0.34 mmol), 3-diethylboranyl-5-d-pyridine (60 mg, 0.41 mmol), bis(triphenylphosphine)palladium (II) chloride (24 mg, 0.03 mmol), and sodium carbonate (132 mg, 1.22 mmol). The reaction solution was reacted at 80° C. for 2 hours. After cooled to room temperature, the reaction was quenched with water (15 mL), filtered through celite, and the filtrate was extracted with ethyl acetate (25 mL×3). The organic layers were combined and the organic layer was washed with brine (30 mL) and dried over anhydrous sodium sulfate. The organic layer was concentrated under reduced pressure and purified by column chromatography (eluate: PE/EtOAc (v/v)=4/1) to give 81 mg of a white solid, yield: 60.2%, purity: 99.32%, LC-MS (APCI): m/z=396.4 (M+1)$^+$. $^1$H NMR (300 MHz, DMSO-d$_6$) (δ/ppm) 8.59 (s, 1H), 8.44 (s, 1H), 7.76 (s, 1H), 6.12 (s, 1H), 5.39 (d, J=3.6 Hz, 1H), 4.60-4.30 (m, 1H), 2.35-2.24 (m, 2H), 2.24-2.14 (m, 1H), 2.12-1.96 (m, 3H), 1.87-1.74 (m, 2H)), 1.72-1.45 (m, 6H), 1.44-1.34 (m, 1H), 1.26-1.11 (m, 1H), 1.09-0.97 (m, 7H).

Example 8 Synthesis of (3β)-17-(3-pyridyl)androst-5,16-dienol-16-d (Compound 34)

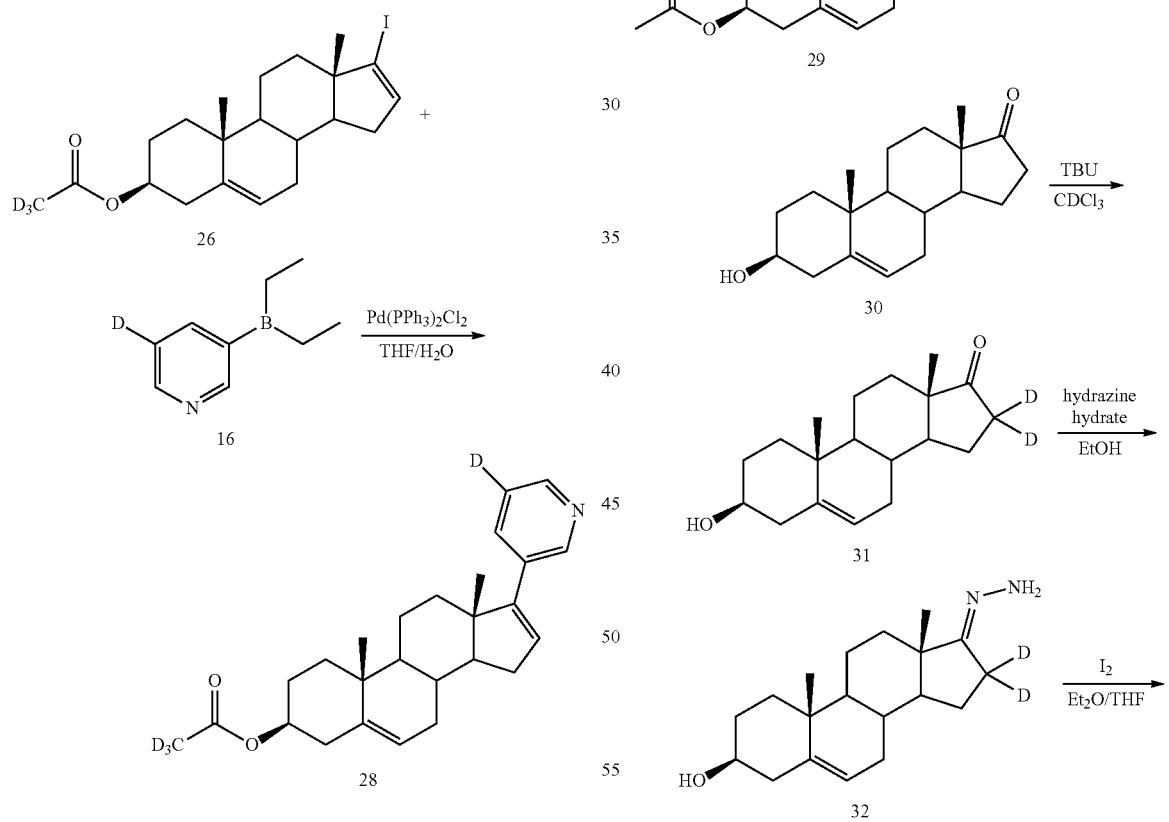

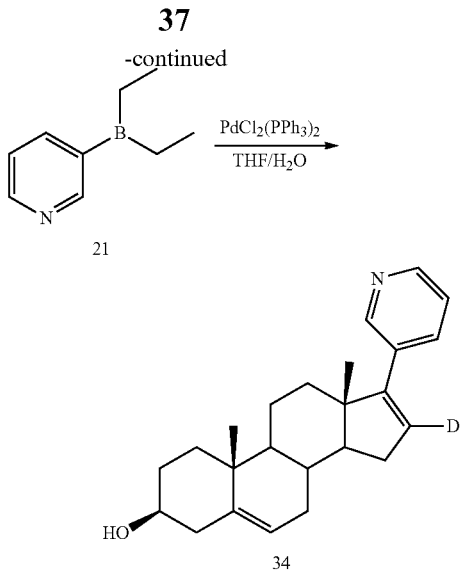

Step 1: Synthesis of Dehydroepiandrosterone (Compound 30)

At room temperature, potassium hydroxide (508 mg, 9.10 mmol) was added to dehydroepiandrosterone acetate (2.50 g, 7.60 mmol) in a mixed solvent of methanol (15 mL) and tetrahydrofuran (5 mL), and reacted at room temperature for 1 hr. The reaction solution was concentrated under reduced pressure, and the residue was dissolved in ethyl acetate (30 mL) and water (30 mL). The layers were separated. The aqueous layer was extracted with ethyl acetate (30 mL×2). The organic layers were combined, washed with brine, dried over anhydrous sodium sulfate, and concentrated under reduced pressure to give 2.39 g of a white solid that was used directly in the next step. LC-MS (APCI): m/z=287.3 (M−1).

Step 2: Synthesis of Dehydroepiandrosterone-16-d2 (Compound 31)

At room temperature, 1,5,7-triazabicyclo(4,4,0)dec-5-ene (TBU) (150 mg, 1.08 mmol) was added to a solution of dehydroepiandrosterone (1.00 g, 3.5 mmol) in deuterated chloroform (15 mL). The reaction was stirred overnight at room temperature. The reaction was quenched with water (30 mL) and extracted with dichloromethane (30 mL×3). The organic layers were combined, washed with saturated brine, dried over anhydrous sodium sulfate, and concentrated under reduced pressure to give 1.00 g of a pale yellow solid which was used directly in the next reaction. LC-MS (APCI): m/z=289.3 (M−1).

Step 3: Synthesis of Dehydroepiandrosterone 17-hydrazone-16-d2 (Compound 32)

At room temperature, to a solution of dehydroepiandrosterone 16-d2 (1.00 g, 3.50 mmol) in ethanol (14 mL) was added hydrazine hydrate (3.00 mL, 60 mmol), and the reaction was heated to reflux and stirred for 1 hour. After cooling to room temperature, water (15 mL) was added and a large amount of a white solid precipitated out of the system. The mixture was filtered under suction and the cake was washed successively with water (3 mL×2) and diethyl ether (3 mL×2) and dried to give 850 mg of a white solid. Yield: 79.9%. LC-MS (APCI): m/z=305.3 [M+1]±.

Step 4: Synthesis of (3β)-17-iodo-androst-5,16-dienol-16-d (Compound 33)

Under an ice bath and nitrogen protection, a solution of dehydroepiandrosterone 17-hydrazone-16-d2 (850 mg, 2.80 mg) in anhydrous tetrahydrofuran (23 mL) was slowly added dropwise (2 hr) to 1,1,3,3-tetramethylguanidine (1.80 g, 15.30 mmol) and elemental iodine (1.42 g, 5.6 mmol) in a mixed solvent of diethyl ether (20 mL) and tetrahydrofuran (41 mL). After completion of the addition, the reaction solution was concentrated under reduced pressure. The residue was dissolved in ethyl acetate (50 mL), washed with water (50 mL) and saturated sodium thiosulfate solution (50 mL), respectively, dried over anhydrous sodium sulfate, and concentrated under reduced pressure to give 1.20 g of a brown-yellow solid, yield: 100%, which is used directly for the next reaction. LC-MS (APCI): m/z=398.2 (M−1).

Step 5: Synthesis of (3β)-17-(3-pyridyl)androst-5,16-dienol-16-d (Compound 34)

At room temperature, under nitrogen protection, a mixed solution of tetrahydrofuran (6 mL) and water (2 mL) was added to a mixture of 17-iodo-androst-5,16-diene-3β-ol-16-d (200 mg, 0.50 mmol), 3-(diethylboryl)pyridine-(88 mg, 0.60 mmol), bis(triphenylphosphine)palladium (II) chloride (20 mg, 0.04 mmol), and sodium carbonate (248 mg, 1.80 mmol), and reacted at 80° C. for 2 hr. After cooled to room temperature, the reaction was quenched with water (25 mL), and filtered through celite, and the filtrate was extracted with ethyl acetate (30 mL×3). The organic layers were combined and the organic layer was washed with brine (30 mL), dried over anhydrous sodium sulfate, and concentrated under reduced pressure and the concentrate was purified by column chromatography (eluent: PE/EtOAc (v/v)=1.5/1) to give 128 mg of a white solid, yield: 73.0%, purity: 99.54%, LC-MS (APCI): m/z=351.3 (M+1). $^1$H NMR (300 MHz, MeOD-d$_4$) (δ/ppm) 8.56 (s, 1H), 8.41 (s, 1H), 7.92 (d, J=8.0 Hz, 1H), 7.44 (dd, J=7.9, 4.9 Hz, 1H), 5.40 (d, J=5.3 Hz, 1H), 3.42 (m, 1H), 2.29 (m, 3H), 2.10 (m, 3H), 1.75 (m, 7H), 1.50 (m, 2H), 1.12 (m, 8H).

Example 9 Synthesis of (3β)-17-(3-pyridyl)androst-5,16-dienyl-16-d d3-acetate (Compound 35)

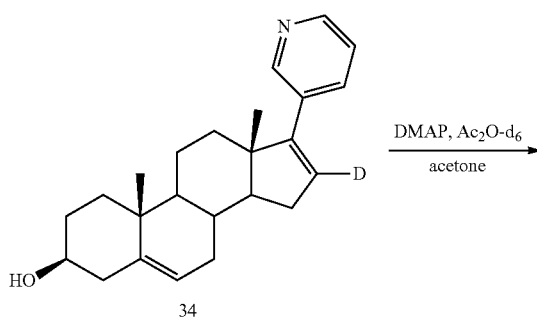

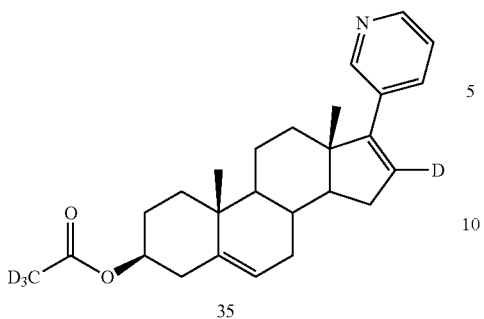

At room temperature, DMAP (4-dimethylaminopyridine) (2.80 mg, 0.02 mmol) was added to a solution of (3β)-17-(3-pyridyl)androst-5,16-dienol-16-d (80 mg, 0.22 mmol) and deuterated acetic anhydride-d6 (58 mg, 0.57 mmol) in acetone (3 mL), and the reaction was stirred at 55° C.-65° C. for 2 hours. The acetone was removed under reduced pressure and 15 mL of water was added to quench the reaction. The reaction was extracted with ethyl acetate (20 mL×3). The combined organic phases were washed with brine, dried over anhydrous sodium sulfate, and concentrated under reduced pressure. The concentrate was purified by column chromatography (eluent: PE/EtOAc (v/v)=3/1) to give 50 mg of a pale yellow solid. Yield: 56.0%, purity: 99.42%, LC-MS (APCI): m/z=396.3 (M+1)$^+$. $^1$H NMR (300 MHz, DMSO-d6) (δ/ppm) 8.59 (s, 1H), 8.43 (d, J=3.6 Hz, 1H), 7.76 (d, J=7.9 Hz, 1H), 7.33 (dd, J=7.7, 4.8 Hz, 1H), 5.39 (d, J=4.1 Hz, 1H), 4.57-4.30 (m, 1H), 2.34-2.24 (m, 2H), 2.24-2.14 (m, 1H), 2.09-1.97 (m, 3H), 1.86-1.73 (m, 2H), 1.71-1.45 (m, 6H), 1.44-1.32 (m, 1H), 1.13-1.07 (m, 1H), 1.07-0.96 (m, 7H).

Example 10 Synthesis of (3β)-17-(3-pyridyl-5-d) androst-5,16-dienyl-16-d d3-acetate (Compound 37)

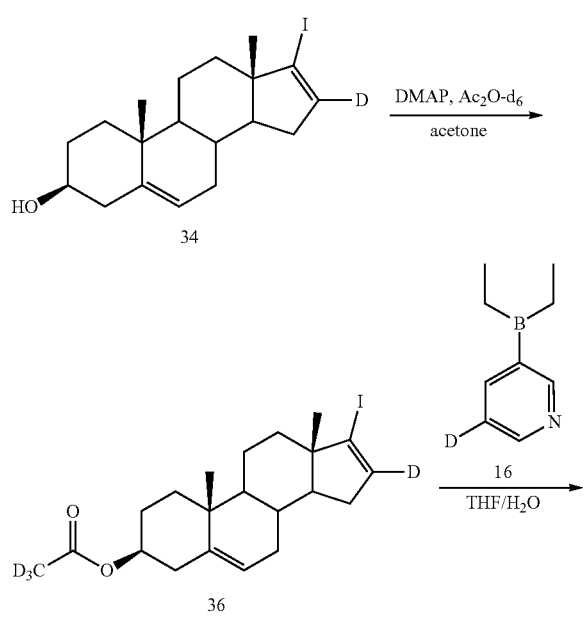

Step 1: Synthesis of (3β)-17-iodoandrost-5,16-dienyl-16-d d$_3$-acetate (Compound 36)

At room temperature, DMAP (4-dimethylaminopyridine) (7.00 mg, 0.06 mmol) was added to a solution of (3β)-17-(3-pyridyl)androst-5,16-dienol-16-d (230 mg, 0.58 mmol) and deuterated acetic anhydride-d6 (176 mg, 0.72 mmol) in acetone (5 mL), and the reaction was stirred at 55° C.-65° C. for 2 hours. The acetone was removed under reduced pressure and 15 mL of water was added to quench the reaction. The reaction was extracted with ethyl acetate (20 mL×3). The combined organic phases were washed with brine, dried over anhydrous sodium sulfate, and concentrated under reduced pressure, and the concentrate was purified by column chromatography (eluent: PE/EtOAc (v/v)=8/1) to give 170 mg of a white solid. Yield: 66.0%, LC-MS (APCI): m/z=445.2 (M+1)$^+$.

Step 2: Synthesis of (3β)-17-(3-pyridyl-5-d)androst-5,16-dienyl-16-d d3-acetate (Compound 37)

At room temperature, under nitrogen protection, a mixed solution of tetrahydrofuran (3 mL) and water (1 mL) was added to a mixture of (3β)-17-iodoandrost-5,16-dienyl-16-d acetate-d$_3$ (80 mg, 0.18 mmol), 3-diethylboranylpyridine-5-d (32 mg, 0.22 mmol), bis(triphenylphosphine)palladium (II) chloride (8.00 mg, 0.03 mmol), and sodium carbonate (69 mg, 0.65 mmol). The reaction solution was reacted at 80° C. for 2 hours. After cooled to room temperature, the reaction was quenched with water (15 mL), filtered through celite, and the filtrate was extracted with ethyl acetate (25 mL×3). The organic layers were combined and the organic layer was washed with brine (30 mL), dried over anhydrous sodium sulfate, and concentrated under reduced pressure. The concentrate was purified by column chromatography (eluent: PE/EtOAc (v/v)=4/1) to afford 60 mg of a white solid, yield: 84.0%, purity: 99.36%, LC-MS (APCI): m/z=397.3 (M+1)$^+$. $^1$H NMR (300 MHz, DMSO-d$_6$) (δ/ppm) 8.58 (s, 1H), 8.42 (s, 1H), 7.75 (s, 1H), 5.38 (d, J=3.8 Hz, 1H), 4.55-4.33 (m, 1H), 2.28 (d, J=7.4 Hz, 2H), 2.24-2.14 (m, 1H), 2.08-1.95 (m, 3H), 1.86-1.72 (m, 2H), 1.71-1.45 (m, 6H), 1.44-1.31 (m, 1H), 1.14-1.06 (m, 1H), 1.06-0.95 (m, 7H).

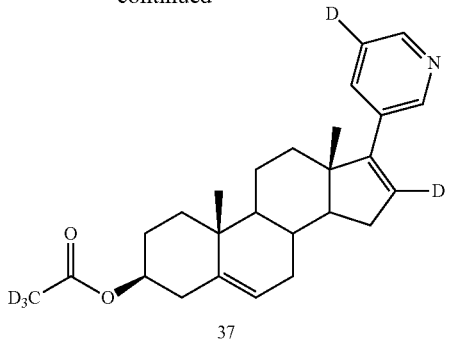

Example 11 Synthesis of (3β)-17-(3-pyridyl-5-d) androst-4,16-dien-3-one (Compound 39)

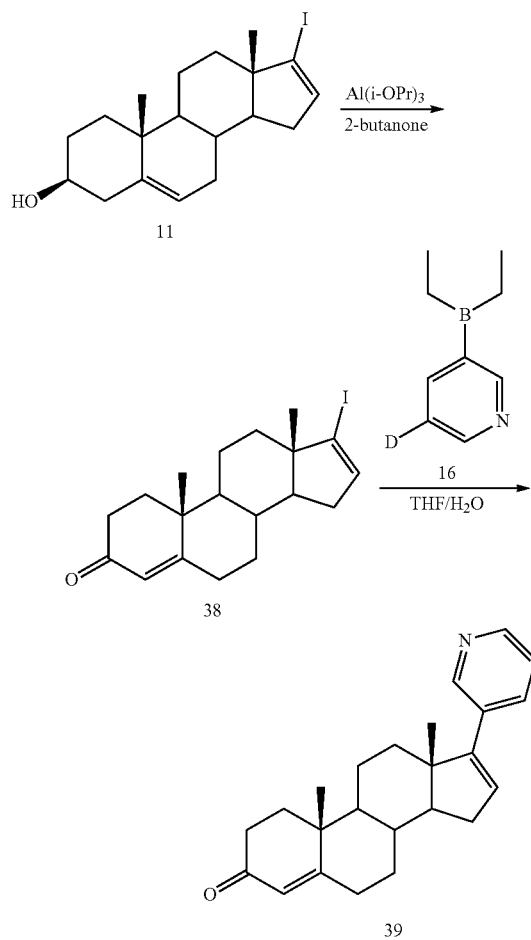

Step 1: Synthesis of 17-iodoandrost-4,16-dien-3-one (Compound 38)

At room temperature, under nitrogen protection, aluminum isopropoxide (Al(i-OPr)₃) (4.61 g, 22.60 mmol) was added to (3β)-17-iodoandrost-5,16-dienol (2.25 g, 5.65 mmol) in a mixed solvent of 2-butanone (20 mL) and toluene (5 mL). The reaction mixture was stirred under reflux for 8 hours. After cooled to room temperature, the reaction was quenched with 40 mL of water and 40 mL of ethyl acetate, and filtered. The filtrate was extracted with ethyl acetate (50 mL×3). The combined organic phases were washed with brine, dried over anhydrous sodium sulfate, and concentrated under reduced pressure and the concentrate was purified by column chromatography (eluent: PE/EtOAc (v/v)=15/1) to give 2.0 g of a white solid. Yield: 91.0%. LC-MS (APCI): m/z=396.6 (M+1).

Step 2: Synthesis of (3β)-17-(3-pyridyl-5-d)androst-4,16-dien-3-one (Compound 39)

At room temperature, under nitrogen protection, a mixed solution of tetrahydrofuran (6 mL) and water (2 mL) was added to a mixture of 17-iodoandrost-4,16-dien-3-one (120 mg, 0.30 mmol), 3-diethylboranylpyridine-5-d (55 mg, 0.36 mmol), bis(triphenylphosphine)palladium (II) chloride (18 mg, 0.02 mmol), and sodium carbonate (100 mg, 0.90 mmol), and the reaction solution was kept at 80° C. overnight (16 hrs). After cooled to room temperature, the reaction was quenched with water (25 mL), and filtered through celite, and the filtrate was extracted with ethyl acetate (30 mL×3). The organic layers were combined and the organic layer was washed with brine (30 mL), dried over anhydrous sodium sulfate, and concentrated under reduced pressure, and the concentrate was purified by column chromatography (eluent: PE/EtOAc (v/v)=2/1) to give 70 mg of a pale yellow solid. Yield: 67%, purity: 96.40%, MS (ESI, pos. ion) m/z: 349.3 (M+1)⁺. ¹H NMR (300 MHz, CDCl₃) (δ/ppm) 8.56 (d, J=44.6 Hz, 2H), 7.66 (s, 1H), 6.01 (s, 1H), 5.77 (s, 1H), 2.54-2.21 (m, 5H), 2.13-1.99 (m, 3H), 1.90-1.52 (m, 8H), 1.25 (s, 3H), 1.20-1.13 (m, 1H), 1.08 (s, 3H).

Example 12 Synthesis of (3β)-17-(3-pyridyl-6-d) androst-4,16-dien-3-one (Compound 40)

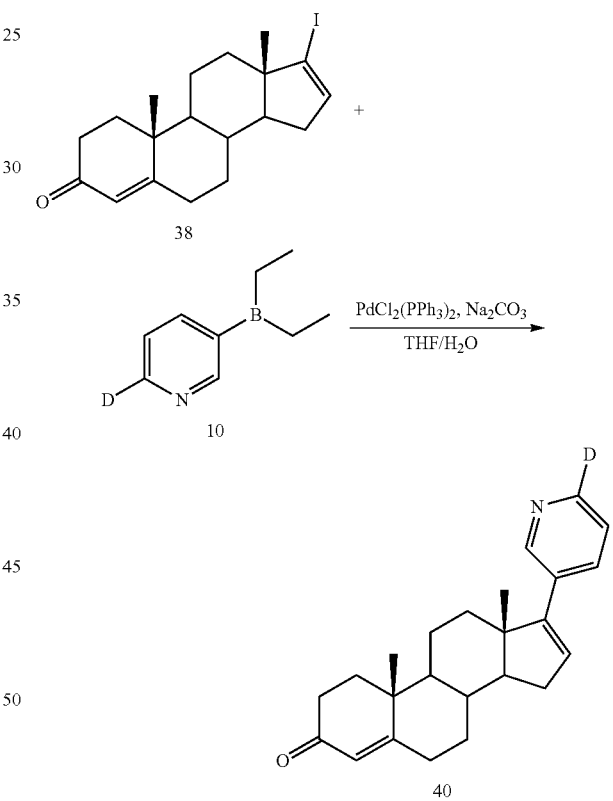

At room temperature, under nitrogen protection, a mixed solution of tetrahydrofuran (6 mL) and water (2 mL) was added to a mixture of 17-iodoandrost-4,16-dien-3-one (120 mg, 0.30 mmol), 3-diethylboranylpyridine-6-d (55 mg, 0.36 mmol), bis(triphenylphosphine)palladium (II) chloride (18 mg, 0.02 mmol), and sodium carbonate (100 mg, 0.90 mmol), and the reaction solution was kept at 80° C. overnight. After cooled to room temperature, the reaction was quenched with water (25 mL), and filtered through celite, and the filtrate was extracted with ethyl acetate (30 mL×3). The organic layers were combined and the organic layer was washed with brine (30 mL), dried over anhydrous sodium sulfate, and concentrated under reduced pressure. The concentrate was purified by column chromatography (eluent: PE/EtOAc (v/v)=2/1) to afford 65 mg of a pale yellow solid. Yield: 64%, purity: 94.70%, LC-MS (APCI): m/z=349.1 (M+1)$^+$. $^1$H NMR (300 MHz, CDCl$_3$) (δ/ppm) 8.53 (d, J=44.2 Hz, 2H), 7.22 (d, J=4.2 Hz, 1H), 5.98 (s, 1H), 5.74 (s, 1H), 2.46-2.23 (m, 5H), 2.09-2.00 (m, 3H), 1.85-1.39 (m, 8H), 1.23 (s, 3H), 1.18-1.11 (m, 1H), 1.05 (s, 3H).

Example 13 Synthesis of (3β)-17-(3-pyridyl)-16-d-androst-4,16-dien-3-one (Compound 41)

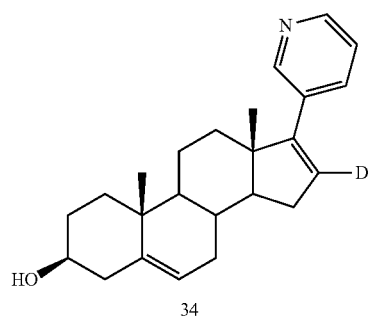

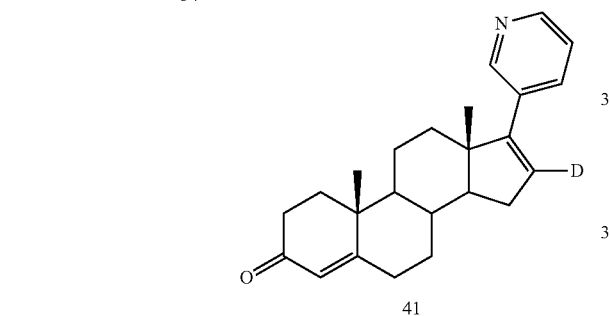

(3β)-17-(3-pyridyl)androst-5,16-dienol-16-d and N-methyl-4-piperidone were dissolved in 14 mL of toluene. After distilling off about 4 mL of toluene with a water separator, the mixture was cooled to room temperature. Under nitrogen protection, aluminum isopropoxide (228 mg, 2.65 mmol) was added to the reaction and the reaction was refluxed overnight. After cooled to room temperature, the reaction was quenched with water (25 mL), and extracted with ethyl acetate (30 mL×3). The organic layers were combined, washed with 5% aqueous sodium bicarbonate solution (30 mL) and brine (30 mL), respectively, dryed over anhydrous sodium sulfate, and concentrated under reduced pressure. The concentrate was purified with column chromatography (eluent: PE/EtOAc (v/v)=1.5/1) to give 76 mg of a white solid, Yield: 59.7%, purity: 96.82%, LC-MS (APCI): m/z=349.3 (M+1)$^+$. $^1$H NMR (300 MHz, MeOD-d$_4$) (δ/ppm) 8.54 (s, 1H), 8.39 (d, J=4.0 Hz, 1H), 7.84 (d, J=8.0 Hz, 1H), 7.38 (dd, J=7.9, 4.9 Hz, 1H), 5.74 (s, 1H), 2.44 (m, 5H), 2.05 (m, 5H), 1.61 (m, 5H), 1.29 (s, 3H), 1.13 (m, 5H).

Example 14 Synthesis of 17-(3-pyridyl-6-d)-2,2-d$_2$-androst-4,16-dien-3-one (Compound 43)

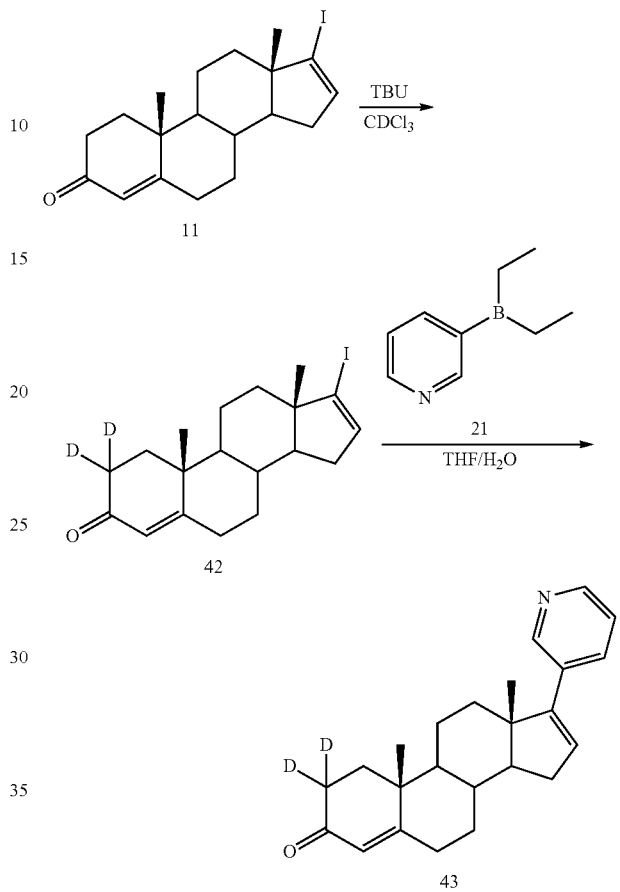

Step 1: Synthesis of 17-iodo-2,2-d$_2$-androst-4,16-dien-3-one (Compound 42)

At room temperature, 1,5,7-triazabicyclo(4,4,0)dec-5-ene (TBU) (20 mg, 0.14 mmol) was added to a solution of 17-iodoandrost-4,16-dien-3-one (200 mg, 0.50 mmol) in deuterated chloroform (30 mL), and the reaction was stirred at room temperature overnight. The reaction was quenched with water (30 mL) and extracted with dichloromethane (30 mL×3). The organic layers were combined, washed with saturated brine, dried over anhydrous sodium sulfate, and concentrated under reduced pressure to give 200 mg of a pale yellow solid which was used directly in the next reaction. LC-MS (APCI): m/z=297.1 (M−1).

Step 2: Synthesis of 17-(3-pyridyl-6-d)-2,2-d$_2$-androst-4,16-dien-3-one

At room temperature, under nitrogen protection, a mixed solution of tetrahydrofuran (6 mL) and water (2 mL) was added to a mixture of 17-iodoandrost-4,16-dien-3-one-2,2-d$_2$ (200 mg, 0.50 mmol), 3-diethylboranylpyridine-6-d (90 mg, 0.60 mmol), bis(triphenylphosphine)palladium (II) chloride (PdCl$_2$(PPh$_3$)$_2$) (30 mg, 0.03 mmol), and sodium carbonate (170 mg, 1.50 mmol), and the reaction solution was kept at 80° C. overnight (16 hrs). After cooled to room temperature, the reaction was quenched with water (25 mL), and filtered through celite, and the filtrate was extracted with ethyl acetate (30 mL×3). The organic layers were combined and the organic layer was washed with brine (30 mL), dried over anhydrous sodium sulfate, and concentrated under reduced pressure and the concentrate was purified by column chromatography (eluent: PE/EtOAc (v/v)=2/1) to give 100 mg of a pale yellow solid. Yield: 58.9%. LC-MS (APCI): m/z=350.3 (M+1)$^+$; $^1$H NMR (300 MHz, MeOD) (δ/ppm) 8.60-8.47 (m, 1H), 8.47-8.30 (m, 1H), 7.91-7.78 (m, 1H), 7.45-7.31 (m, 1H), 6.17-6.01 (m, 1H), 5.75-5.71 (m, 1H), 2.63-2.26 (m, 3H), 2.23-2.08 (m, 2H), 2.07-1.86 (m, 3H), 1.75-1.44 (m, 5H), 1.29 (s, 3H), 1.20-1.03 (m, 5H).

Example 14 Inhibition of CYP17 Enzyme

CYP17 Lyase Assay

Human CYP17 was expressed in HEK293 cells and microsome were prepared, which was subsequently used as a source of enzyme for lyase assays. The reaction includes 200 nM [3H]-hydroxy pregnenolone (ARC), 200 nM 17-hydroxy pregnenolone (Sigma), 2 mM NADPH (Calbiochem), and CYP 17-HEK293 microsomes, which were incubated for 20 minutes at room temperature in the presence of DMSO or a test compound. Compounds were dissolved in DMSO and serially diluted. The reaction was stopped by the addition of 0.2N HCl and the product was captured using an anti-mouse YSi SPA Bead (GE) conjugated anti-DHEA monoclonal antibody (Abcam). The signal intensity determined by Packard Top Count was used to calculate the percent inhibition and IC50 values.

CYP17 Hydroxylase Assay

E. coli was transformed to express active human CYP17, and a membrane prepared from the transformed E. coli was used as a source of the enzyme. The reaction was performed in a 50 uL final volume solution containing 200 nM hCYP17 membrane, 25 μM pregnenolone (Sigma), 7 mM NADPH (Calbiochem), 1 μM cytochrome P450 reductase (Invitrogen) and 50 mM sodium phosphate buffer pH 7.3. The IC50 of compounds dissolved in 100% DMSO was determined by serial dilution of assay buffer to a final concentration of 0.2% DMSO. The reaction mixture was incubated at 37° C. for 120 minutes and 200 μL of 0.02 N HCl in acetonitrile was added to stop the reaction. The sample was then spun at 750,000 g and 200 μL of the supernatant was transferred to a clean tube for determination. The reaction product 17-alpha pregnenolone was measured by LC/MS.

The inhibition effects of the examples of the present disclosure on CYP17 were shown in Table 1 below:

TABLE 1

Inhibition effects of example compounds on CYP17 enzyme

| Number | CYP17 lyase IC50 (μM) | CYP17 hydroxylase IC50 (μM) |
|---|---|---|
| Example 1 | <0.01 | <0.02 |
| Example 2 | <0.01 | <0.02 |
| Example 3 | <0.01 | <0.02 |
| Example 4 | <0.01 | <0.02 |
| Example 5 | <0.01 | <0.02 |
| Example 6 | <0.01 | <0.02 |
| Example 7 | <0.01 | <0.02 |
| Example 8 | <0.01 | <0.02 |
| Example 9 | <0.01 | <0.02 |
| Example 10 | <0.01 | <0.02 |
| Example 11 | <0.01 | <0.02 |
| Example 12 | <0.01 | <0.02 |

TABLE 1-continued

Inhibition effects of example compounds on CYP17 enzyme

| Number | CYP17 lyase IC50 (μM) | CYP17 hydroxylase IC50 (μM) |
|---|---|---|
| Example 13 | <0.01 | <0.02 |
| Abiraterone | <0.01 | — |

From the above table, it can be seen that the compound of the present disclosure has a high inhibitory activity against the CYP17 enzyme (activity is comparable to that of abiraterone) and thus can be used as a drug for treating a CYP17-related disease such as prostate cancer.

Example 15 Inhibition of Cellular PSA Protein Secretion

Experimental steps: 1. The original culture medium was replaced with culture medium containing 10% Charcoal Stripped FBS, and cells were allowed to starve in culture flasks for 24 hours; 2. Cells were digested and counted, and LNcaP cells were seeded into 96-well plates at 10,000 cells/well and incubated overnight; 3. The DHT and compound were added to the existing medium at a set concentration, the final concentration of DHT was 1 nM, the initial concentration of the compound was 50000 nM, 5-fold dilution was carried out, 8 concentration gradients were obtained, and incubation was carried out for 48 hours; 4. Cell culture supernatants were collected and PSA protein levels were measured according to the ELISA kit instructions. IC50 was calculated using GraphPad Prism based on the inhibition rate at each concentration, and the results were shown in Table 2 below.

TABLE 2

Inhibition of cellular PSA proteins by example compounds

| Number | Inhibition of PSA proteins, IC50 (μM) |
|---|---|
| Example 11 | <0.01 |
| Example 12 | <0.01 |
| Example 13 | <0.01 |

From the above table, it can be seen that the compounds of the present disclosure have a high inhibitory activity against the cell PSA protein and thus can be used as a drug for treating prostate cancer.

Example 16 Pharmacokinetic Evaluation in Rats 8 male Sprague-Dawley rats (7-8 weeks old, and weighing approximately 210 g) were divided into two groups with 4 rats in each group, a single oral dose of 5 mg/kg given to the two groups were (a) control group: (3β)-17-(3)-pyridyl)androst-5,16-dienol and (b) test group: Examples 1-13, and pharmacokinetic differences between the two groups were compared.

The rats were raised on standard food and water. Fasting was started 16 hours before the test. The drug was dissolved with PEG400 and dimethyl sulfoxide. The blood samples were collected from eyelids at the time points of 0.083 hours, 0.25 hours, 0.5 hours, hour, 2 hours, 4 hours, 6 hours, 8 hours, 12 hours, and 24 hours after administration.

Rats were briefly anesthetized after inhalation of diethyl ether and 300 μL of blood sample was collected from the eyelids into test tubes. There was 30 μL of 1% heparin salt solution in the test tube. Tubes were dried at 60° C. overnight before use. After the blood sample was collected at a later time point, the rats were sacrificed after ether anesthesia.

Immediately after the collection of the blood sample, the test tube was gently inverted at least 5 times to ensure sufficient mixing and then placed on ice. The blood sample was centrifuged at 5000 rpm at 4° C. for 5 minutes to separate the plasma from the red blood cells. 100 μL of plasma was aspirated into a clean plastic centrifuge tube with a pipette, marking with the name of the compound and time point. Plasma was stored at −80° C. prior to analysis. The concentration of the compound of the present disclosure in plasma was determined by LC-MS/MS. The pharmacokinetic parameters were calculated based on the blood concentration of each animal at different time points.

TABLE 3

Rat pharmacokinetics experiment

| PK parameters | Abiraterone acetate | | Example 5 | | Example 9 | |
|---|---|---|---|---|---|---|
| | IV | PO | IV | PO | IV | PO |
| $T_{max}$ (h) | 2.00 | 1.33 | 3.00 | 1.67 | 17.33 | 1.67 |
| $C_{max}$ (h) | 10.6 | 505.9 | 24.1 | 813.2 | 43.6 | 549.0 |
| $AUC_{0-t}$ (h * ng/mL) | 109.8 | 1287.7 | 224.1 | 2424.0 | 797.6 | 2481.5 |
| $AUC_{0-\infty}$ (h * ng/mL) | 192.1 | 1320.6 | 273.9 | 2435.5 | 591.1 | 2546.3 |

The experimental results were shown in Table 3. Compared to abiraterone acetate, the compounds of the present disclosure showed better pharmacokinetics both in oral and intraperitoneal administration (significant increase in $C_{max}$, and significant increase in AUC data), and thus the present compound has better pharmacodynamics and therapeutic effects in animals.

Example 17 Metabolic Stability Evaluation

Experiments in microsomes: Human liver microsomes: 0.5 mg/mL, Xenotech; Coenzyme (NADPH/NADH): 1 mM, Sigma Life Science; Magnesium chloride: 5 mM, 100 mM phosphate buffer (pH 7.4).

Preparation of stock solution: Powder of the example compound was accurately weighed and dissolved in DMSO to 5 mM.

Preparation of phosphate buffer (100 mM, pH7.4): A pre-formulated 0.5M potassium dihydrogen phosphate (150 mL) was mixed with 0.5M dibasic potassium phosphate (700 mL). The pH of the mixture was adjusted to 7.4 with 0.5M dibasic potassium phosphate solution. The mixture was diluted 5-fold with ultrapure water before use, and magnesium chloride was added to obtain a phosphate buffer (100 mM) containing 100 mM potassium phosphate, 3.3 mM magnesium chloride, pH 7.4.

A NADPH regeneration system solution (containing 6.5 mM NADP, 16.5 mM G-6-P, 3 U/mL G-6-P D, 3.3 mM magnesium chloride) was prepared and placed on wet ice prior to use.

Preparation of stop solution: acetonitrile solution containing 50 ng/mL propranolol hydrochloride and 200 ng/mL tolbutamide (internal standard). 25057.5 μL of phosphate buffer (pH 7.4) was taken into a 50 mL centrifuge tube, to which 812.5 μL human liver microsomes were added, and mixed to obtain a liver microsome dilution solution with a protein concentration of 0.625 mg/mL. 25057.5 μL of phosphate buffer (pH 7.4) was taken into a 50 mL centrifuge tube, to which 812.5 μL SD rat liver microsomes were added, and mixed to obtain a liver microsome dilution solution with a protein concentration of 0.625 mg/mL.

Incubation of the samples: The stock solution of the respective compound was respectively diluted to 0.25 mM with an aqueous solution containing 70% acetonitrile, and used as a working solution, ready for use. 398 μL of the dilution solution of human liver microsomes or rat liver microsome were added to a 96-well incubation plate (N=2), respectively, and 2 μL of 0.25 mM working solution was added and mixed.

Metabolic stability assay: 300 μL of pre-chilled stop solution was added to each well of a 96-well deep well plate and placed on ice as a stop plate. The 96 well incubation plate and NADPH regeneration system were placed in a 37° C. water bath box, shaken at 100 rpm and pre-incubated for 5 min. 80 μL of incubation solution was taken out from each well of the incubation plate and added to the stop plate, mixed, and replenished with 20 μL of NADPH regeneration system solution as a 0-min sample. 80 μL of NADPH regeneration system solution was added to each well of the incubation plate to start the reaction and start counting. The corresponding compound had a reaction concentration of 1 μM and the protein concentration was 0.5 mg/mL. Separately, 100 μL of the reaction solution was taken at 10, 30, and 90 min reaction, respectively, added to a stop plate, and vortexed for 3 minutes to terminate the reaction. The stop plate was centrifuged at 5000×g at 4° C. for 4 min. 100 μL of the supernatant was added to a 96-well plate to which 100 μL of distilled water was previously added, mixed, and analyzed by LC-MS/MS.

Data analysis: The peak areas of the corresponding compound and internal standard were detected by LC-MS/MS system, and the ratio of the peak area of the compound to the internal standard was calculated. The slope was measured by plotting the natural logarithm of the percent of compound remaining versus time, and $t_{1/2}$ and $CL_{int}$ were calculated according to the formula, where V/M is equal to 1/protein concentration.

The compounds of the examples were analyzed according to the above procedure. The results were shown in Table 2.

TABLE 4 metabolism of Examples 1, 2 and 8 in Human liver microsome

| Number | $t_{1/2}$ (min) | $CL_{int}$ (μL/min/mg) |
|---|---|---|
| abiraterone | 40.0 | 34.7 |
| abiraterone metabolite | 2.1 | 646.7 |
| Example 1 | >145 | <9.6 |
| Example 2 | 71.2 | 19.5 |
| Example 8 | 51.3 | 24.3 |
| Example 12 | 3.4 | 407.5 |

As shown in Table 4, compared to the non-deuterated compound, the deuterated abiraterone (Examples 1, 2, 8) and the deuterated abiraterone metabolite (Example 12) of the present disclosure have prolonged half-life and reduced clearance, indicating that the compounds of the present disclosure can significantly improve metabolic stability.

TABLE 5

Metabolism of metabolized abiraterone in Examples 3, 4, 5, 7 and 9 in human liver microsome

| Number | Analyte/IS max | Analyte/IS mini | $t_{1/2}$ (min) |
|---|---|---|---|
| Abiraterone acetate | 2.188 | 0.075 | 25 |
| Example 3 | 0.155 | 0.007 | 30 |
| Example 4 | 0.213 | 0.009 | 30 |
| Example 5 | 0.646 | 0.036 | 25 |
| Example 7 | 0.896 | 0.031 | 28 |
| Example 9 | 1.116 | 0.047 | 30 |

Abiraterone acetate as a prodrug of abiraterone can be rapidly metabolized to abiraterone, so the metabolism of metabolized abiraterone of the prodrug in liver microsomes was measured. As shown in Table 5 above, the half-life of the deuterated prodrug (Examples 3, 4, 7 and 9) was significantly prolonged, indicating that the prodrug of the compound of the present disclosure can also improve the metabolic stability.

The above content is a further detailed description of the present disclosure in combination with specific preferred embodiments, and it cannot be assumed that the specific implementation of the present disclosure is limited to these descriptions. For a person of ordinary skill in the art to which the present disclosure belongs, a number of simple deductions or substitutions can be made without departing from the concept of the present disclosure, and should all be considered as falling within the protection scope of the present disclosure.

What is claimed is:

1. A compound represented by Formula (I),

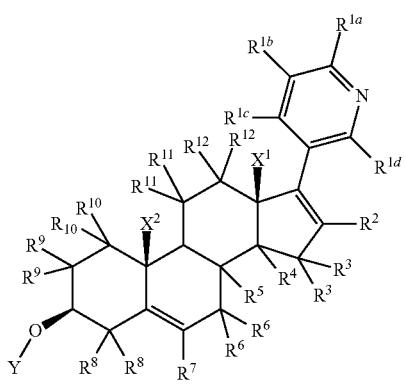

Formula (I)

wherein $R^{1a}$, $R^{1b}$, $R^{1c}$, $R^{1d}$, and $R^2$ are each independently hydrogen, deuterium, or halogen; $R^3$, $R^4$, $R^5$, $R^6$, $R^7$, $R^8$, $R^9$, $R^{10}$, $R^{11}$ and $R^{12}$ are each independently hydrogen, halogen, or trifluoromethyl;

$X^1$ and $X^2$ are methyl;

Y is selected from hydrogen (H), acetyl, and an acetyl group substituted with one or more deuteriums;

and pharmaceutically acceptable salts, solvates, hydrates, polymorphs, tautomers and stereoisomers thereof, including mixtures of these compounds in all ratios;

wherein the compound does not include non-deuterated compounds.

2. The compound according to claim 1, wherein $R^{1a}$, $R^{1b}$, $R^{1c}$, and $R^{1d}$ are each independently deuterium or hydrogen.

3. The compound according to claim 1, wherein at least one of $R^{1a}$, $R^{1b}$, $R^{1c}$, and $R^{1d}$ is deuterium.

4. The compound according to claim 1, wherein $R^3$, $R^4$, $R^5$, $R^6$, $R^7$, $R^8$, $R^9$, $R^{10}$, $R^{11}$ and $R^{12}$ are hydrogen.

5. The compound according to claim 1, wherein $R^2$ is deuterium.

6. The compound according to claim 5, wherein Y is an acetyl group substituted with three deuteriums.

7. The compound according to claim 1, wherein Y is selected from hydrogen, and an acetyl group substituted with one or more deuteriums.

8. The compound according to claim 1, wherein Y is an acetyl group substituted with three deuteriums.

9. The compound according to claim 1, which is selected from the group consisting of the following compounds or pharmaceutically acceptable salts thereof:

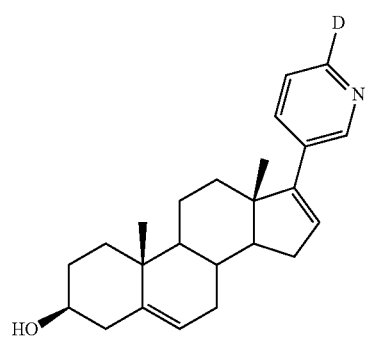

Formula (2)

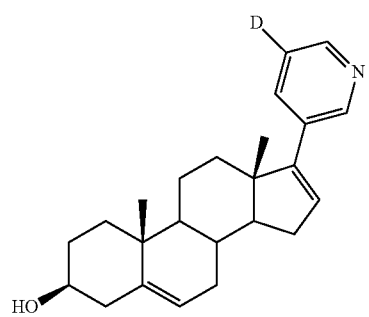

Formula (3)

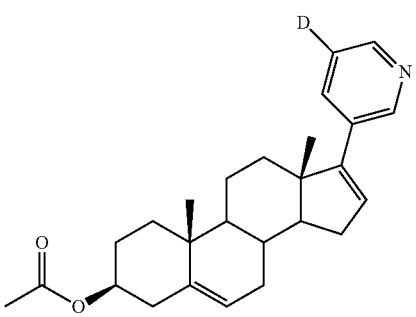

Formula (4)

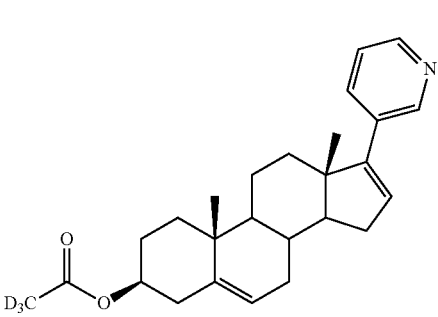

Formula (5)

Formula (6)
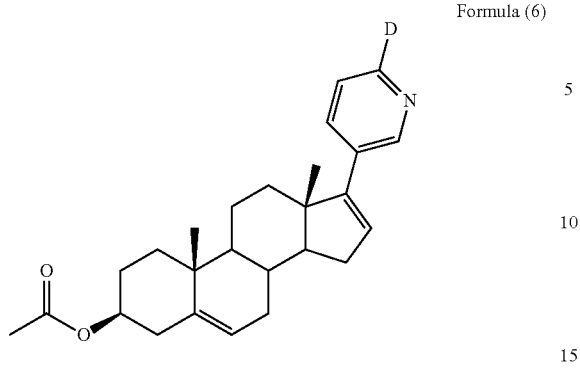
Formula (7)
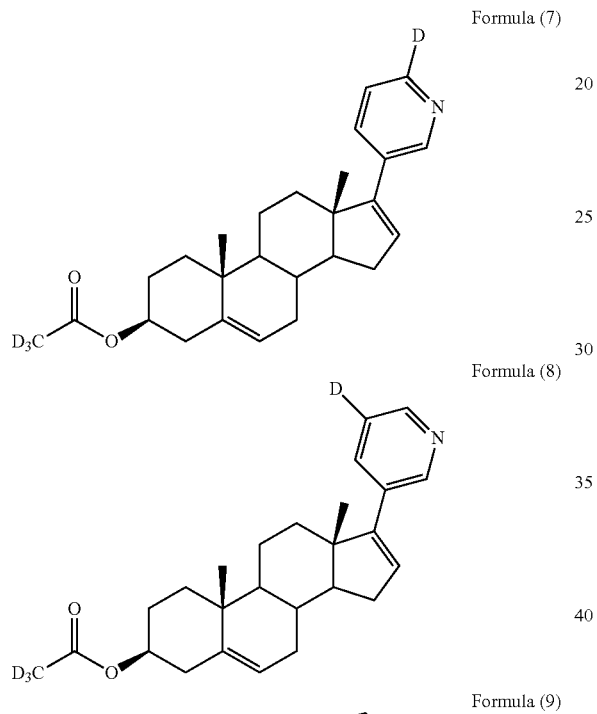
Formula (8)
Formula (9)
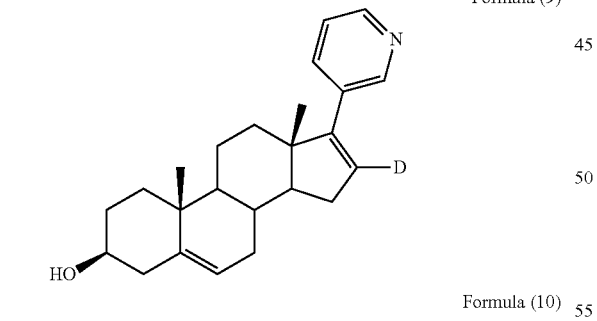
Formula (10)
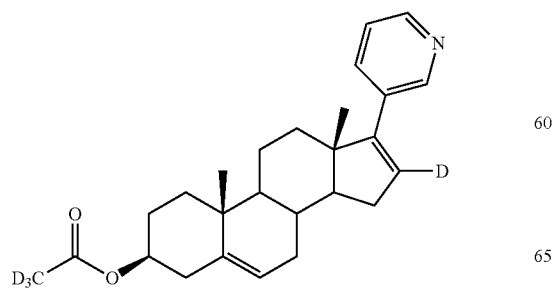
Formula (11)
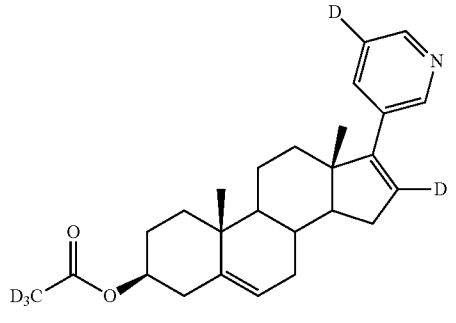
Formula (12)
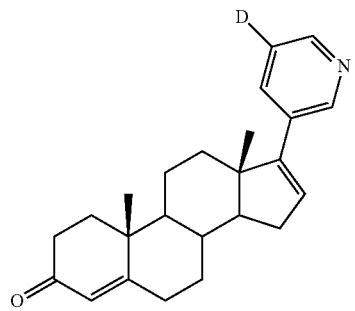
Formula (13)
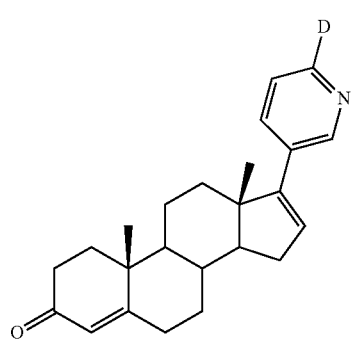
Formula (14)
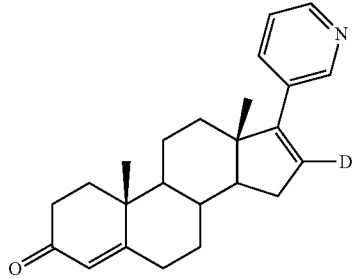
Formula (15)
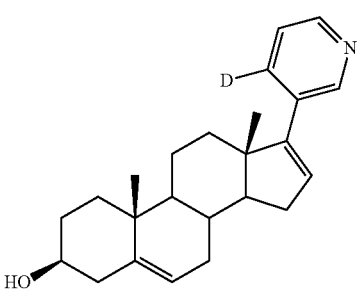

Formula (16)
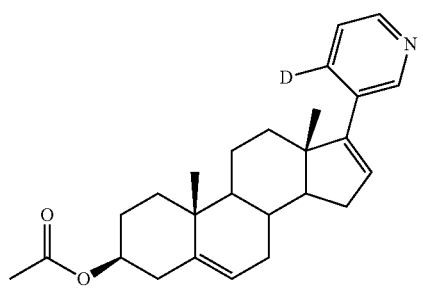
Formula (17)
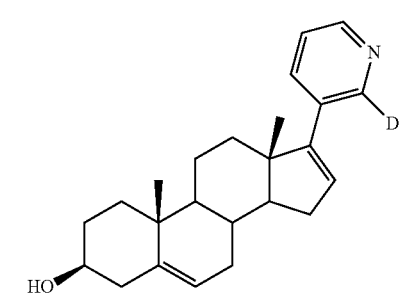
Formula (18)
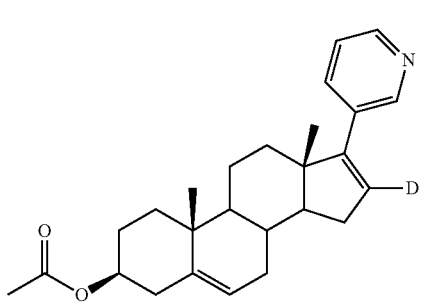
Formula (21)
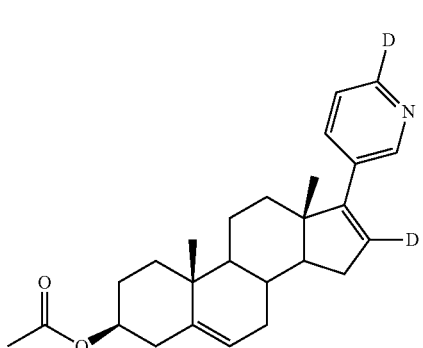
Formula (46)
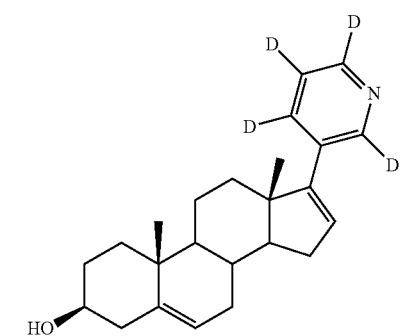
Formula (47)
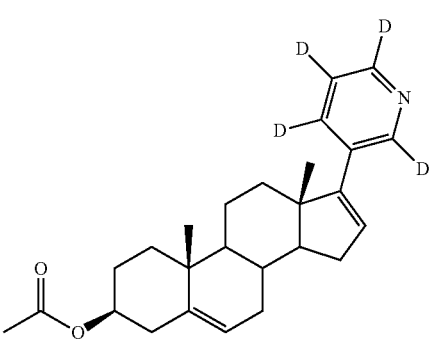
Formula (48)
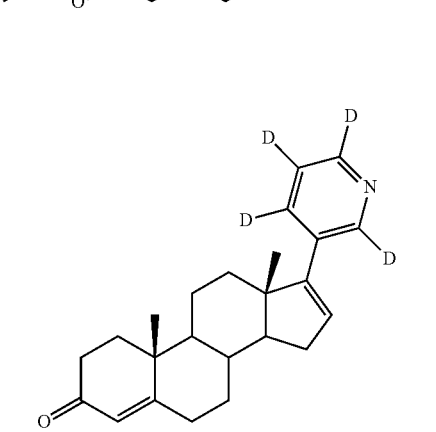
Formula (51)
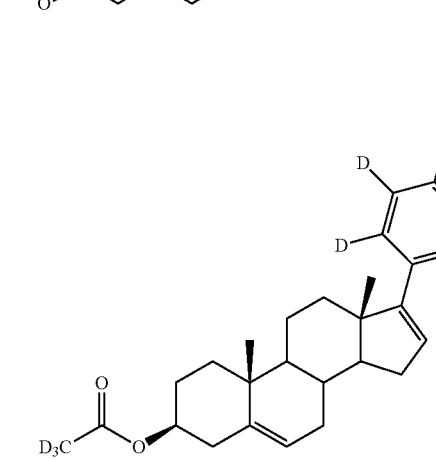
10. A compound, which is:
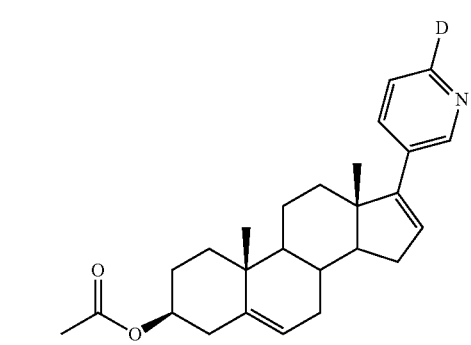 [SMILES: [2H]c1ccc(C2=CCC3C4CC=C5C[C@@H](OC(C)=O)CC[C@]5(C)C4CC[C@]23C)cn1]
or a pharmaceutically acceptable salt thereof.

11. A compound, which is:

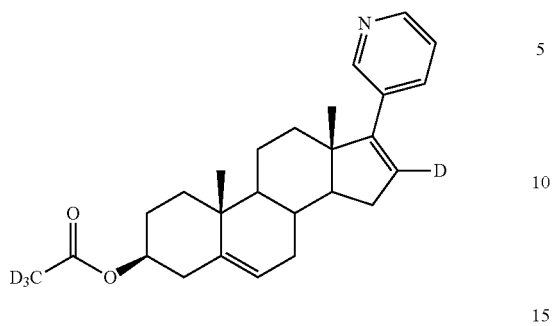

or a pharmaceutically acceptable salt thereof.

12. A pharmaceutical composition comprising: the compound according to claim 1 or a pharmaceutically acceptable salt thereof; and a pharmaceutically acceptable carrier.

13. A method for treating prostate cancer in a subject, comprising administering to said subject the compound of Formula (I) according to claim 1 or a polymorph, pharmaceutically acceptable salt, stereoisomer, hydrate or solvate thereof.

14. A method for treating prostate cancer in a subject, comprising administering to said subject the pharmaceutical composition according to claim 12.

* * * * *